(12) United States Patent
Wilson et al.

(10) Patent No.: US 11,022,718 B2
(45) Date of Patent: Jun. 1, 2021

(54) SYSTEM, METHOD AND APPARATUS FOR DETERMINING THE DISPOSITION OF STRUCTURAL FEATURES PRESENT IN BOREHOLE CORES

(71) Applicant: Imdex Global B.V., Zuidoost (NL)

(72) Inventors: Grant Alexander Wilson, Sandton (ZA); John David Wilson, Sandton (ZA); Martin Muller, Kensington (ZA)

(73) Assignee: Imdex Global B.V., Amsterdam (NL)

( * ) Notice: Subject to any disclaimer, the term of this patent is extended or adjusted under 35 U.S.C. 154(b) by 268 days.

(21) Appl. No.: 15/549,302

(22) PCT Filed: Feb. 10, 2016

(86) PCT No.: PCT/IB2016/000106
§ 371 (c)(1),
(2) Date: Aug. 7, 2017

(87) PCT Pub. No.: WO2016/128820
PCT Pub. Date: Aug. 18, 2016

(65) Prior Publication Data
US 2018/0024269 A1    Jan. 25, 2018

(30) Foreign Application Priority Data
Feb. 10, 2015    (ZA) .................................. 2015/00960

(51) Int. Cl.
*G01V 99/00* (2009.01)
*G01N 33/24* (2006.01)
(52) U.S. Cl.
CPC ............. *G01V 99/00* (2013.01); *G01N 33/24* (2013.01)
(58) Field of Classification Search
CPC ............................... G01N 33/24; G01V 99/00
See application file for complete search history.

(56) References Cited

U.S. PATENT DOCUMENTS 4,542,648 A * 9/1985 Vinegar ................ E21B 49/005
                                                         73/152.07
5,437,104 A * 8/1995 Chien .................... G03B 17/06
                                                         33/266

(Continued)

FOREIGN PATENT DOCUMENTS

| AU | 722965 | 8/2000 |
|---|---|---|
| EP | 1 345 422 | 9/2003 |
| WO | WO 2007/102129 | 9/2007 |

OTHER PUBLICATIONS

International Search Report dated Aug. 29, 2016 (6 pages) out of PCT priority Application No. PCT/IB2016/000106.

(Continued)

*Primary Examiner* — Kyle R Quigley
(74) *Attorney, Agent, or Firm* — Felix L. Fischer

(57) ABSTRACT

A system method and apparatus for determining the disposition or orientation of a structural feature or structural feature present in a borehole core, such as a core sample. The apparatus is provided to capture data on structural features present in the core sample. The apparatus includes an orientation arrangement configured to determine the orientation, or change in orientation, of the apparatus, and a data-capturing arrangement configured to capture orientation data generated by the orientation arrangement. The orientation arrangement may include a gyroscope. The apparatus also includes an alignment arrangement operable to align the apparatus with a structural feature relating to the core sample. The alignment arrangement may include an alignment indicator operable to provide visual indication on the surface of the core sample. The method may include real-time delivery of data from the point of acquisition to cloud-based storage.

29 Claims, 14 Drawing Sheets

(56) References Cited

U.S. PATENT DOCUMENTS

| | | | |
|---|---|---|---|
| 2002/0029128 A1 | 3/2002 | Jones | |
| 2009/0080705 A1* | 3/2009 | Orpen | G01N 33/24 382/109 |
| 2010/0155599 A1* | 6/2010 | Godavarty | A61B 5/0091 250/334 |
| 2014/0086381 A1 | 3/2014 | Grader | |
| 2014/0328454 A1 | 11/2014 | Zarra | |
| 2016/0194940 A1* | 7/2016 | Andersen | E21B 43/00 703/2 |

OTHER PUBLICATIONS

Written Opinion of the International Preliminary Examining Authority (PCT Rule 66) dated Mar. 15, 2017 (14 pages) out of PCT priority Application No. PCT/IB2016/000106.

Written Opinion of the International Searching Authority (PCT Rule 43bis.I) dated Aug. 29, 2016 (11 pages) out of PCT priority Application No. PCT/IB2016/000106.

Paulsen et al., "A simple method for orienting drill core by correlating features in whole-core scans and oriented borehole-wall imagery", Journal of Structural Geology, vol. 24, No. 8, Aug. 2002, pp. 1233-1238, NPL Reference No. XP055204054.

* cited by examiner

| Borehole Survey details | | | Coordinates | | | Planes | | Calculated planar orientation details | | | | | | Section | | Linear Feature measurements | | | | | Calculated linear orientation details | | |
|---|---|---|---|---|---|---|---|---|---|---|---|---|---|---|---|---|---|---|---|---|---|---|---|
| No | Depth | Dip | Azimuth | Size | Dia. unit T/B | X | Y | Z | LEFT | RIGHT | mid-point | alpha | beta | ID | Dip | Directi | Bearing | App.dip | End-A | RA-A | End-B | RA-B | mid-point gamma | ID | Plunge | Trend |
| 1 | 2.600 | -89.0 | 256.0 | NQ | 4.76 cm B | 12345.30 | 6567.20 | 1657.00 | 0 | -0.8 | 2.596 | 76.6 | 135.0 | f1 | 12.7 | -66.1 | 234.0 | 5.0 | 4.78 | 340 | 24 | 279 | 2.596 76.6 | Fold1 | -16.3 | 256.1 |
| 2 | 5.400 | -89.0 | 256.0 | NQ | 4.76 cm B | 12345.30 | 6567.20 | 1657.00 | 0.8 | -0.9 | 5.400 | 70.3 | 93.4 | f1 | 19.7 | -107.4 | 0.0 | -5.5 | | | | | 5.400 70.3 | | | |
| 3 | 11.740 | -89.0 | 256.0 | NQ | 4.76 cm B | 12345.30 | 6567.20 | 1657.00 | 0.9 | -1.2 | 11.739 | 66.0 | 98.1 | f1 | 23.9 | -102.1 | 0.0 | -4.5 | | | | | 11.739 66.0 | | | |
| 4 | 13.500 | -89.0 | 256.0 | NQ | 4.76 cm B | 12345.30 | 6567.20 | 1657.00 | 1.1 | -1.7 | 13.497 | 59.0 | 102.1 | f1 | 30.8 | -97.6 | 0.0 | -3.3 | | | | | 13.497 59.0 | | | |
| 5 | 14.850 | -89.0 | 256.0 | NQ | 4.76 cm B | 12345.30 | 6567.20 | 1657.00 | 0 | -.2 | 14.840 | 59.3 | 135.0 | f1 | 30.0 | -64.2 | 0.0 | 11.1 | | | | | 14.840 59.3 | | | |
| 6 | 18.350 | -89.0 | 256.0 | NQ | 4.76 cm B | 12345.30 | 6567.20 | 1657.00 | .3 | -1.5 | 18.329 | 47.5 | 164.1 | f2 | 41.6 | -1.7 | 0.0 | 41.5 | | | | | 18.329 47.5 | | | |
| 7 | 20.750 | -89.0 | 256.0 | NQ | 4.76 cm B | 12345.30 | 6567.20 | 1657.00 | .3 | -1.3 | 20.730 | 47.5 | 159.9 | f2 | 41.6 | 2.5 | 0.0 | 41.5 | | | | | 20.730 47.5 | | | |
| 8 | 23.300 | -89.0 | 256.0 | NQ | 4.76 cm B | 12345.30 | 6567.20 | 1657.00 | .2 | -.8 | 23.287 | 59.6 | 165.5 | f2 | 29.4 | -3.0 | 0.0 | 29.4 | | | | | 23.287 59.6 | | | |
| 9 | 28.000 | -89.0 | 256.0 | NQ | 4.76 cm B | 12345.30 | 6567.20 | 1657.00 | .7 | 1.1 | 27.995 | 17.6 | 93.8 | f3 | 72.4 | -104.5 | 0.0 | -4.3 | | | | | 27.995 17.6 | | | |
| 10 | 30.650 | -89.0 | 256.0 | NQ | 4.76 cm B | 12345.30 | 6567.20 | 1657.00 | .3 | 1.4 | 30.628 | 45.1 | 161.6 | f2 | 43.9 | 0.8 | 0.0 | 43.9 | | | | | 30.628 45.1 | | | |
| 11 | 33.920 | -89.0 | 256.0 | NQ | 4.76 cm B | 12345.30 | 6567.20 | 1657.00 | .0 | 1.5 | 33.913 | 70.1 | 144.5 | f1 | 18.9 | -55.7 | 0.0 | 10.1 | | | | | 33.913 70.1 | | | |
| 12 | 35.500 | -89.0 | 256.0 | NQ | 4.76 cm B | 12345.30 | 6567.20 | 1657.00 | -1 | -1 | 35.487 | 60.4 | 177.9 | f1 | 28.3 | -20.5 | 0.0 | 25.8 | | | | | 35.487 60.4 | | | |
| 13 | 36.300 | -89.0 | 256.0 | NQ | 4.76 cm B | 12345.30 | 6567.20 | 1657.00 | 4 | 4.3 | 36.338 | 32.3 | 3.8 | b1 | 59.1 | 165.3 | 0.0 | -49.9 | | | | | 36.338 32.3 | | | |
| 14 | 37.250 | -89.0 | 256.0 | NQ | 4.76 cm B | 12345.30 | 6567.20 | 1657.00 | -2 | .2 | 37.234 | 53.3 | 158.5 | f2 | 35.3 | 3.7 | 0.0 | 35.1 | | | | | 37.234 53.3 | | | |
| 15 | 40.550 | -89.0 | 256.0 | NQ | 4.76 cm B | 12345.30 | 6567.20 | 1657.00 | 0.6 | -1 | 40.577 | 34.8 | -37.9 | b1 | 56.8 | 123.9 | 0.0 | -16.8 | | | | | 40.557 34.8 | | | |
| 16 | 40.100 | -89.0 | 256.0 | NQ | 4.76 cm B | 12345.30 | 6567.20 | 1657.00 | .3 | .3 | 40.080 | 46.8 | -153.4 | f2 | 41.4 | 8.6 | 0.0 | 40.4 | | | | | 40.080 46.8 | | | |
| 17 | 41.200 | -89.0 | 256.0 | NQ | 4.76 cm B | 12345.30 | 6567.20 | 1657.00 | .3 | -1.6 | 41.177 | 44.0 | -162.3 | f2 | 43.9 | -0.8 | 0.0 | 43.9 | | | | | 41.177 44.0 | | | |
| 18 | 43.950 | -89.0 | 256.0 | NQ | 4.76 cm B | 12345.30 | 6567.20 | 1657.00 | -1.5 | -3.3 | 43.974 | 42.9 | -20.6 | b1 | 49.9 | 140.7 | 0.0 | -28.3 | | | | | 43.974 42.9 | | | |
| 19 | 44.950 | -89.0 | 256.0 | NQ | 4.76 cm B | 12345.30 | 6567.20 | 1657.00 | 1.2 | -1.5 | 44.949 | 60.3 | 96.3 | f1 | 29.5 | -108.9 | 0.0 | -8.1 | | | | | 44.949 60.3 | | | |
| 20 | 46.100 | -89.0 | 256.0 | NQ | 4.76 cm B | 12345.30 | 6567.20 | 1657.00 | 0.5 | -1 | 46.098 | 71.6 | 108.4 | f1 | 17.6 | -101.7 | 0.0 | -3.3 | | | | | 46.098 71.6 | | | |

Fig. 14

SYSTEM, METHOD AND APPARATUS FOR DETERMINING THE DISPOSITION OF STRUCTURAL FEATURES PRESENT IN BOREHOLE CORES

This application claims priority to International Application No. PCT/IB2016/000106 filed Feb. 10, 2016 and to South African Application No. 2015/00960 filed Feb. 10, 2015; the entire contents of each are incorporated herein by reference.

This invention relates to determination of the disposition/orientation of a structural feature or structural feature present in a borehole core.

BACKGROUND OF THE INVENTION

The following discussion of the background art is intended to facilitate an understanding of the present invention only. The discussion is not an acknowledgement or admission that any of the material referred to is or was part of the common general knowledge as at the priority date of the application.

Diamond drilling involves the excavation of sections of drill core underground in order to determine the underground geology.

Techniques for determining the orientations/dispositions of structures present in borehole cores are widely known and used. However, existing techniques are for the most part awkward, time consuming and often require specialised training for effective and reliable structural analysis.

The existing techniques typically involve measurements taken to represent the borehole are the depth of a section of core extracted, as well as the direction that the section of core faces in three dimensions. If the directions were to be known as a function of the depth, then the path that the borehole traces out in three dimensions can be derived. The borehole survey typically gives the direction as a function of measured depths.

There are several structural features that generally require measurement; namely, linear structural features, planar structural features, or a combination of both (e.g. striations on shear surfaces). Planar structural features may include: bedding, cleavage, foliations, joints, faults and the like. Linear structural features may include features such as slickenside striae, fold axes, crenulations, mullions, deformed pebbles, and the like.

These features are typically measured on a core sample by a geologist who records the data and later logs it for subsequent analysis. The measurements are taken using conventional instruments, such as a rule to measure distance and a goniometer to measure angles. The measurements, once taken, are recorded and later logged for subsequent analysis. This can be a time-consuming procedure which involves several steps at which errors might possibly occur.

It is against this background that the present invention has been developed.

In particular, the present invention in one embodiment seeks to provide an arrangement by which the orientation of planar and linear structural features relative to a core can be determined by utilising one apparatus.

SUMMARY OF THE INVENTION

In accordance with a first aspect of the invention there is provided a method of determining the disposition/orientation of structural feature(s) present in a borehole core, wherein the method includes:

moving/orienting an apparatus, or part thereof, in a specific relation to a structural feature present in the core;

capturing data on the movement/orientation of the apparatus, or said part thereof, as/when it is moved/oriented in relation to the structural feature and core, by using a movement/orientation arrangement of the apparatus; and determining, by using a processor, the orientation/disposition of the structural feature in relation to the core, by utilising the captured data.

The method may further include visually displaying the orientation/disposition of the structural feature in relation to the core on a display.

The method may also include transferring data relating to the orientation/disposition of the structural feature in relation to the core to a remote server. In this regard, the method may include real-time delivery of data from the point of acquisition to cloud-based storage.

The core may be a core sample.

More specifically, the step of determining the orientation/disposition of the structural feature includes determining the real space orientation/disposition in relation to the core.

For the purposes of the specification, the term "structural features" refers to linear structural features, planar structural features, or a combination of both (e.g. striations on shear surfaces). Planar structural features may include: bedding, cleavage, foliations, joints, faults, and the like. Linear structural features may include features such as slickenside striae, fold axes, crenulations, mullions, deformed pebbles, and the like.

The method may be performed outside an actual borehole (e.g. in a testing/analysing environment, such as a test lab).

The step of moving/orienting an apparatus may include aligning the apparatus, or a part thereof, with the structural feature, or a specific part/portion thereof.

The step of determining the orientation of the structural feature in relation to the core may include determining the movement/orientation of the apparatus in relation to a reference point/orientation. The method may therefore include determining a reference point/orientation for the apparatus. The reference point/orientation may be in relation to the core.

A core typically has an elongate, cylindrical shape. A longitudinal side of the core therefore refers to a radially outer side of the core which extends between opposed ends thereof. An outer surface of the core refers to the surface of the longitudinal side. The reference orientation may therefore, for instance, be where the apparatus (or part thereof) is placed against an outer surface of the core. More specifically, the reference orientation may be where the apparatus (or part thereof) is placed against the outer surface and oriented along the length thereof (e.g. along a bottom-of-core line).

The step of moving/orienting the apparatus may include, if the structural feature is a planar feature, aligning the apparatus, or said part thereof, with a surface of the feature. More specifically, the method may include aligning the apparatus, or part thereof, with the surface by aligning an alignment indicator with the surface of the feature. The alignment indicator may comprise means for providing a visual indication on the surface of the core sample. The alignment indicator may comprise a beam of light which is projected from the apparatus to the surface. The beam may be a laser beam. Accordingly, the method may include the step of aligning the apparatus, or a part thereof, with the surface by aligning a beam of light which is projected from the apparatus with the surface.

The step of moving/orienting the apparatus may include moving the apparatus over an outer surface of the core in order to align the apparatus, or part thereof, with at least one part of the structure which is exposed on the outer surface, and to capture orientation data of the apparatus once aligned. More specifically, the step of capturing the data may include aligning the apparatus, or part thereof, with two or more parts of the structure which are exposed on the outer surface, and to each time capture orientation data once aligned.

The method may include determining, by using a processor, the change in orientation of the apparatus, or a part thereof, between a reference orientation and the orientation when it is aligned with the structure, or said part thereof.

The capturing/measuring of structural features using the apparatus may therefore be made directly off the surface of the core. The apparatus may therefore have the ability to measure the orientation of structures accurately even at relatively high core angles relative to the core axis (i.e. to record the orientation of non-penetrative linear structural features, such as fold axes and crenulations).

The step of visually displaying the orientation/disposition of the structural feature may more specifically include displaying the orientation/disposition of the said structural feature in real time as soon as the data has been captured and the orientation/disposition of the structural feature in relation to the core sample has been determined. The real-space orientation of structures is therefore immediately (i.e. in real time) presented to the geologist at the time of logging/capturing the data.

As mentioned above, there may be provision for transfer of data from the point of acquisition to cloud-based storage.

In accordance with a second aspect of the invention there is provided apparatus for capturing data on structural features present in a borehole core, wherein the apparatus includes:

an orientation arrangement which is configured to determine the orientation, or change in orientation, of the apparatus, or part thereof;

a data-capturing arrangement which is configured to capture orientation data generated by the orientation arrangement.

The apparatus may include an alignment arrangement which can be used to align the apparatus with a structural feature, when in use. In other words, the alignment arrangement is operable to align the apparatus with the structural feature. The alignment arrangement may comprise an alignment indicator.

The alignment indicator may comprise means for providing a visual indication on the surface of the core sample.

The alignment indicator may comprise a beam-forming arrangement which is configured to emit at least one beam, when in use, which can be used to align the apparatus with the structural feature. The beam-forming arrangement may be configured to emit a single beam or two beams. The, or each of the, beams may be a light beam. The light beam may more specifically be a laser beam.

The data-capturing arrangement may include at least one data-capturing button which can be used to capture specific orientation data of the current orientation of the apparatus.

The orientation arrangement may include a gyroscope. In addition, the orientation arrangement may include an accelerometer and/or optical sensor.

The apparatus may include a magnetometer.

The apparatus may include a communication arrangement which is configured to send orientation data to a processing arrangement. More specifically, the communication arrangement may be configured to send orientation data wirelessly to a processing arrangement.

The apparatus may include a user interface having a display. More specifically, the apparatus may optionally also include a mouse wheel, or a switch (e.g. a capacitive switch), which is configured to allow for easy scrolling through menu options provided on the display, when in use.

The apparatus may include a housing within which at least part of the orientation arrangement is housed.

The apparatus may be a handheld apparatus.

The apparatus may include at least one guide formation which is configured to guide displacement of the apparatus over an outer surface of a borehole core, when in use. More specifically, the apparatus may include a pair of guide formations.

The movement over an outer surface of a borehole core may comprise displacement along the outer surface in a direction parallel to the core axis. With this arrangement, the displacement comprises rectilinear motion and the apparatus moves in a straight path over the outer surface. In other words, the motion is in one dimension.

Alternatively, or additionally, the movement may comprise displacement around the outer surface about the central longitudinal axis; that is, the movement may comprise a circular motion over the outer surface.

In accordance with a third aspect of the invention there is provided a system for determining the disposition/orientation of structural features present in a borehole core, wherein the system includes:

an apparatus configured to derive data on a structural feature present in a borehole core, from the core;

a processing arrangement which is connected to, or forms part of, the apparatus, and which is configured to determine at least the orientation of the structural feature in relation to the borehole core, by utilising at least the derived data.

The system may also include provision of a visual simulation of the orientation of the structural feature in relation to the borehole core by utilising a display arrangement.

The display arrangement may form part of the system.

The system may also include provision for transfer of data to cloud-based storage. In this regard, the system may have provision for real-time delivery of data from the point of acquisition using the apparatus to cloud-based storage accessible. This may allow visibility of the data in real time from anywhere (for example from a remote office), enabling effective decision making and minimising risks of operational delays. It may also assist in minimising the risk of human error in the transfer of the data.

The processing arrangement may be configured to provide the visual simulation in real-time, as soon as the orientation of the structural feature in relation to the borehole core has been determined. By providing the simulation in real-time, a user is able to obtain immediate feedback on the structural features which were captured.

The apparatus may be configured to derive data on a structural feature present in a borehole core, from a sample of the core.

The apparatus may be an apparatus in accordance with the second aspect of the invention.

In accordance with a fourth aspect of the invention there is provided a method of providing a visual simulation/illustration of a borehole core, wherein the method includes:

receiving orientation data from an apparatus, wherein the data relates to at least one structural feature present in the core;

determining, by using a processor, at least the orientation of the structural feature in relation to the borehole core, by utilising the received data; and displaying a visual simulation/illustration of the structural feature in relation to the borehole core on a display, by utilising the determined orientation.

The orientation data may be received wirelessly from the apparatus.

The apparatus may be an apparatus in accordance with the second aspect of the invention.

More specifically, the step of receiving orientation data may include:

receiving orientation data on a reference orientation; and receiving orientation data related to at least one structural feature present in the core.

The step of determining the orientation of the structural feature may include utilising both the orientation data on the reference orientation and the orientation data related to the at least one structural feature.

The steps of determining the orientation of the structural feature and displaying the visual simulation may be conducted in real-time.

The structural feature may be a linear feature or a planar feature.

In accordance with a fifth aspect of the invention there is provided an apparatus for collecting data relating to a structural feature present in a core sample having a circular outer periphery defining an outer surface and a central longitudinal axis defining a core axis, the apparatus comprising a body configured for engagement with an outer surface of the core sample, the body comprising a base portion adapted for movement over the outer surface to determine the distance between two measurement points on the outer surface, the body further comprising an alignment indicator presenting a reference for aligning the body with a plane transverse to the central longitudinal axis, whereby an indication of the angular disposition of the plane can be obtained by a determination of the attitude of the apparatus relative to the central longitudinal axis.

The movement over the outer surface may comprises a sliding movement over the outer surface.

The movement over the outer surface may comprise displacement along the outer surface in a direction parallel to the central longitudinal axis. With this arrangement, the displacement comprises rectilinear motion and the apparatus moves in a straight path over outer surface. In other words, the motion is in one dimension.

Alternatively, or additionally, the movement may comprise displacement around the outer surface about the central longitudinal axis; that is, the movement may comprise a circular motion over the outer surface. This may measure angular displacement between two measurement points on the outer surface which are angularly offset.

The circular motion may involve subjecting the base portion to both a displacement and a rotation. In this arrangement, the apparatus moves in a curved path over outer surface. In other words, the motion is in two or three dimensions, depending upon the path along which the base portion is moved. In one arrangement, the two points may each be in a respective plane normal to the central longitudinal axis, with the two planes spaced axially along the core sample, in which case the displacement may comprise displacement along the outer surface in a direction parallel to the central longitudinal axis and also displacement around the outer surface about the central longitudinal axis. In another arrangement, the two points may be in a common plane normal to the central longitudinal axis, in which case the displacement may comprise only circular motion.

The body may further comprise a contact portion for contacting the outer surface of the core sample while moving the body angularly with respect to the central longitudinal axis of the core sample to align the body with a plane transverse to the central longitudinal axis. With this arrangement, the contact portion may provide a reference point on the outer surface at which the indication of the angular disposition of the plane is obtained. Further, the contact portion may function to stabilise the body with respect to the core sample as it is moved angularly with respect to the central longitudinal axis of the core sample.

The alignment indicator may comprise means for providing a visual indication on the surface of the core sample.

In operation, the attitude of the body is varied so as to align the visual indication with the structural feature being assessed.

The alignment indicator may comprise one or more light emitting devices for projecting light onto the outer surface of the core sample to provide said visual indication on the surface of the core sample.

The light emitting devices may comprise means for emitting coherent radiation such as a laser beam.

Other forms of indication are also contemplated, such as for example an electro-mechanical indicator. The electro-mechanical indicator may comprise an alignment marker such as an angularly adjustable limb extending from the body and adapted to be manually aligned with a structural feature of the cores sample being assessed, with the electro-mechanical indicator providing an output indicative of the angle of the structural feature relative to the central longitudinal axis of the core sample.

The base portion may be configured as a saddle for location on an outer surface of the core sample and sliding movement over the outer surface.

The saddle may be adapted to cooperate with the core sample for guided movement over the outer surface, including in particular axially along the outer surface.

The body may further comprise a locator for positioning the base portion with respect to a mark or feature an outer surface of the core sample. The locator may comprise a point provided on the base portion. The locator may be integrated with the contact portion.

The apparatus may be configured as a hand-held tool.

In accordance with a sixth aspect of the invention there is provided a method of capturing data on structural features present in a borehole core, the method comprising use of apparatus according to the fifth aspect of the invention.

BRIEF DESCRIPTION OF THE DRAWINGS

The invention will now be described, by way of example, with reference to the accompanying diagrammatic drawings. In the drawings:

FIG. 14 shows an example of a data file of the system in accordance with the invention, displaying the various parameters obtained by the system that can be exported to an Excel spreadsheet;

In the drawings like structures are referred to by like numerals throughout the several views. The drawings shown are not necessarily to scale, with emphasis instead generally being placed upon illustrating the principles of the present invention.

The figures depict several embodiments of the invention. The embodiments illustrate certain configurations; however, it is to be appreciated that the invention can take the form of many configurations, as would be obvious to a person skilled in the art, whilst still embodying the present invention. These configurations are to be considered within the scope of this invention.

DESCRIPTION OF PREFERRED EMBODIMENTS

As mentioned, diamond drilling involves the excavation of sections of drill core underground in order to determine the underground geology. The measurements typically taken to represent the borehole are the depth of a section of core extracted, as well as the direction that the section of core faces in three dimensions. If the directions were to be known as a function of the depth, then the path that the borehole traces out in three dimensions can be derived. The borehole survey typically gives the direction as a function of measured depths. A unit vector pointing along this direction is derived, and is interpolated for intermediate values of the depth. When parameterised in this way, the integral of the unit vector with respect to the downhole depth gives the location of the borehole in three dimensions. The current system, in accordance with the invention, allows the orientation of planar and linear structural features relative to a core to be determined by utilising a geotechnical, electronic handheld apparatus.

Figure 21:
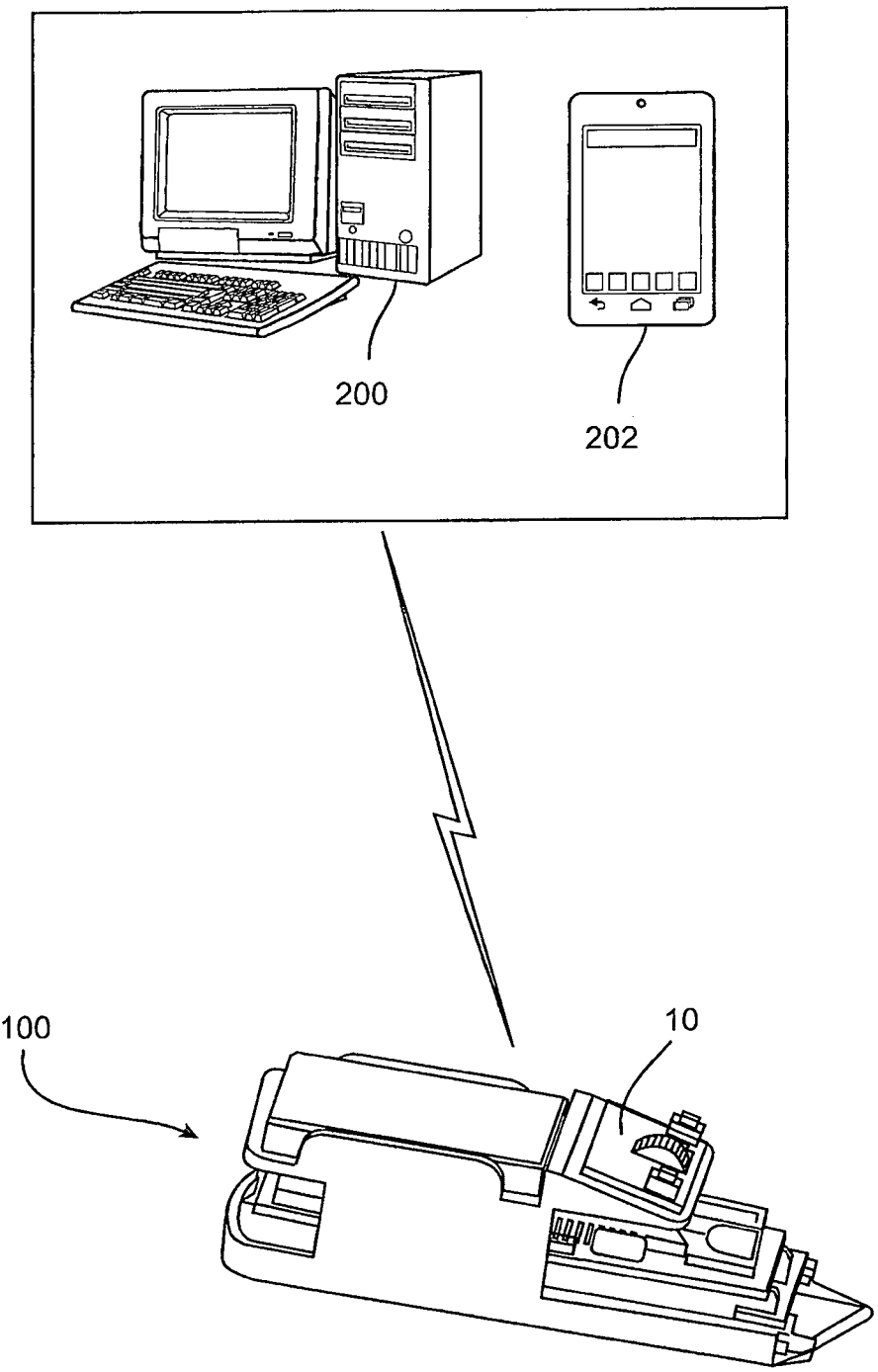
FIG. 21 shows a schematic layout of a system in accordance with the invention.

In the drawings, reference numeral 100 refers generally to a system for determining the disposition/orientation of structural features present in a borehole core (see FIG. 21). The system 100 includes, amongst others, a geotechnical, electronic handheld apparatus 10 and a central computer 200 or similar communications enabled computing device such as a personal computing device, a PDA, a web enable mobile phone, a web enable computer tablet or the like. In the arrangement shown, the communications enabled computing device is depicted in the form of tablet computer 202 which is connected wirelessly to the apparatus 10.

The system 100 may provide for transfer of data from the point of acquisition to cloud-based storage. In this regard, the sub-system 100 may have provision for real-time delivery of data from the point of acquisition using apparatus 10 to cloud-based storage accessible from a remote office. This may allow visibility of the data in real time from anywhere, enabling effective decision making and minimizing risks of operation delays. It also minimises the risk of human error in the transfer of the data. The cloud-based storage may be of any appropriate form; including, for example, a data management and storage system known as Reflex™ Hub™

The apparatus (10) comprises an orientation arrangement configured to determine the orientation, or change in orientation, of the apparatus, and a data-capturing arrangement configured to capture orientation data generated by the orientation arrangement, as will become apparent later.

Figure 1:
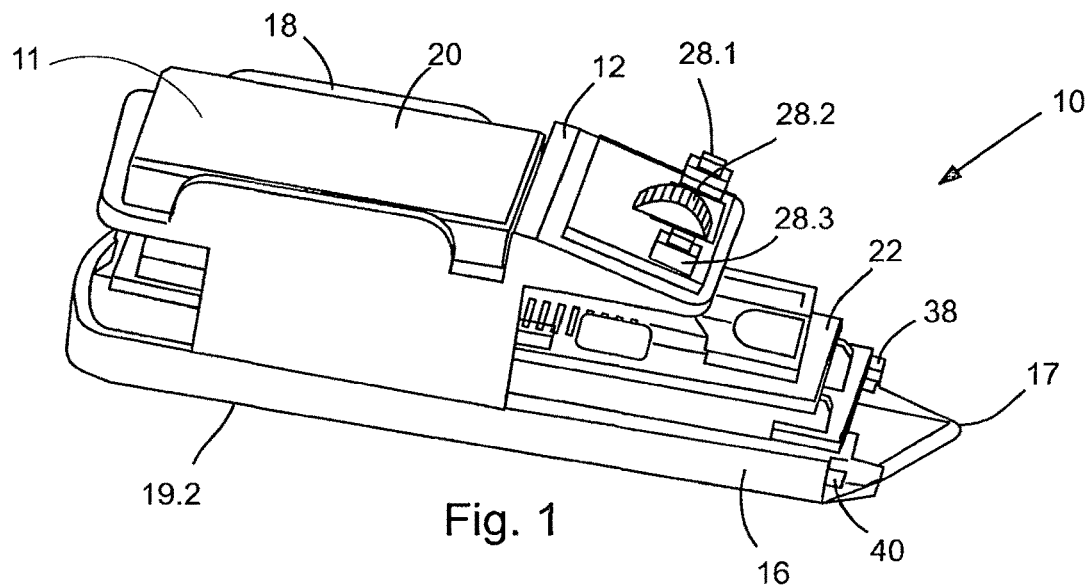
FIG. 1 shows schematically a three-dimensional view of a first embodiment of an apparatus in accordance with the invention, without an outer casing.
Figure 20:
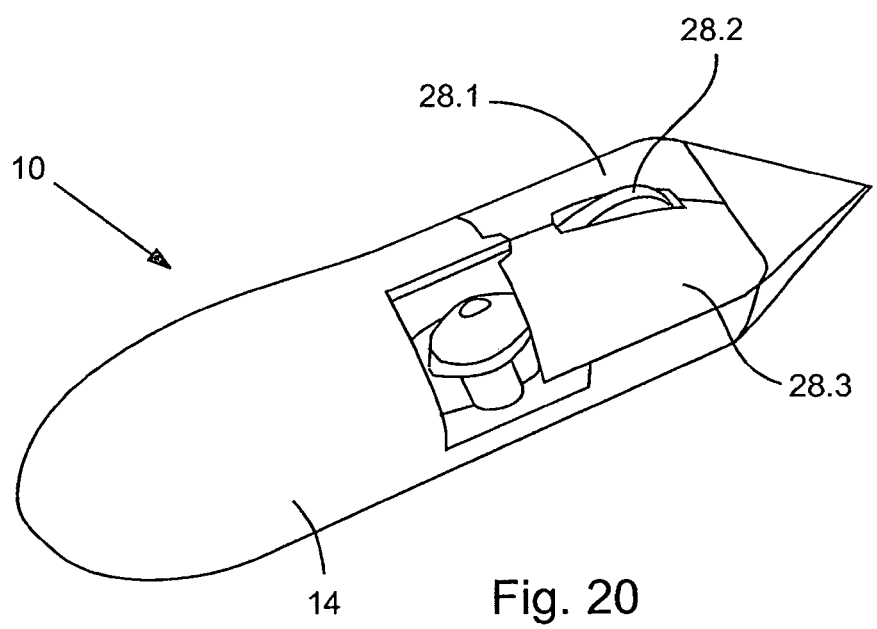
FIG. 20 shows another three-dimensional view of the apparatus of FIG. 19.

The apparatus 10 comprises a body 11 having an inner casing/housing 12 and an outer casing 14 (see FIG. 1 as well as FIGS. 20 and 21) which at least partially encloses the inner casing 12. The inner casing 12 includes a bracket formation 18 within which a battery pack 20 and a charging USB port are housed at the back of the apparatus, a GPS unit (not specifically shown), and activations means 28. A printed circuit board (PCB) 22 is housed in the inner casing 12.

Figure 3:
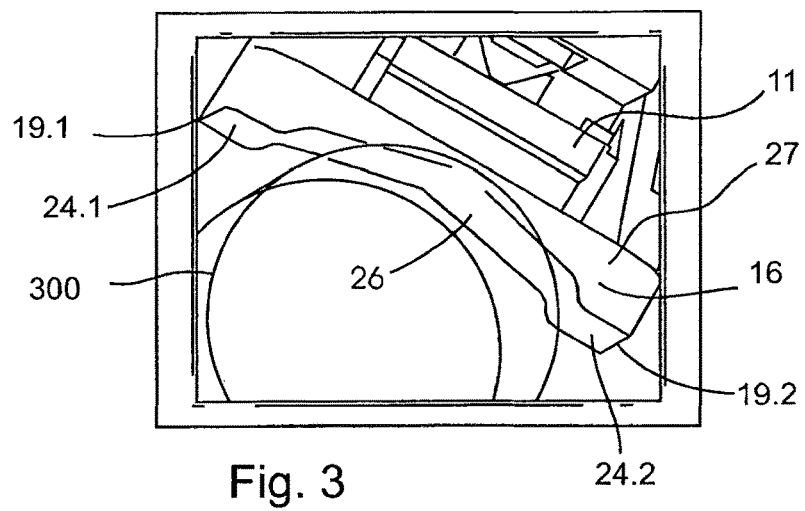
FIG. 3 shows a three-dimensional view of part of the apparatus of FIG. 1, when viewed from below showing the reference surfaces for measuring the structure exposed on surfaces in the core.
Figure 9:
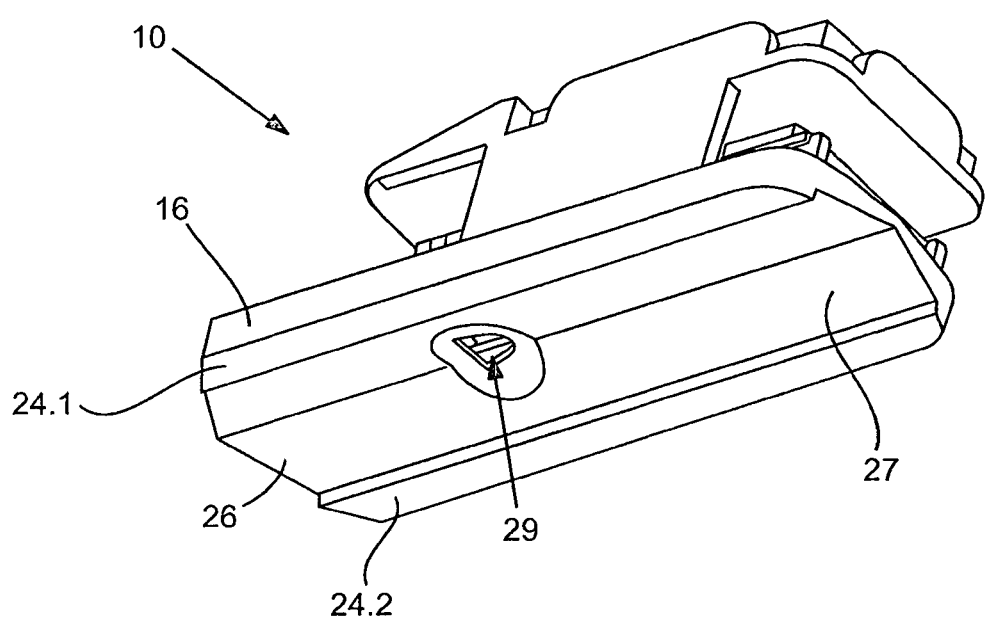
FIG. 9 shows a three-dimensional view of the apparatus of FIG. 1, when viewed from below, displaying an optical sensor prism protruding through a base of the apparatus.

The inner casing 12 has an elongate base 16 which includes two parallel, elongate guide formations 24.1, 24.2 (see FIGS. 3 and 9). An operatively lower part 26 of the elongate base 16 is configured to define a saddle 27. In the arrangement shown, the lower part 26 is concave (or otherwise recessed) and has a generally obtusely angled V-shape, when seen in end view (see FIG. 3). The angle of the V-shape may be about 146° to accommodate a range of typical core diameters.

A front part of the base 16 tapers into a point 17. The point 17 can be used to position the apparatus 10 at a specific depth marker on an outer surface 400 of a core 300, and to locate the position on the surface 400 of the core 300 where a planar/liner structural feature is exposed on the surface 400. In this way, the point 17 provides locator which can be positioned with respect to a mark or feature apparent on the outer surface 400 of a core 300. In other words, the point 17 defines what is, in effect, a cursor.

The saddle 27 is adapted for location on the surface 400 of the core 300 and to cooperate with the core 300 for guided movement over the core surface. In particular, opposed lateral sides of the base 16, which form the guide formations 24.1, 24.2, have straight edges 19.1, 19.2 in order to help the apparatus 10 to be aligned with exposed linear structural features.

Figure 15:
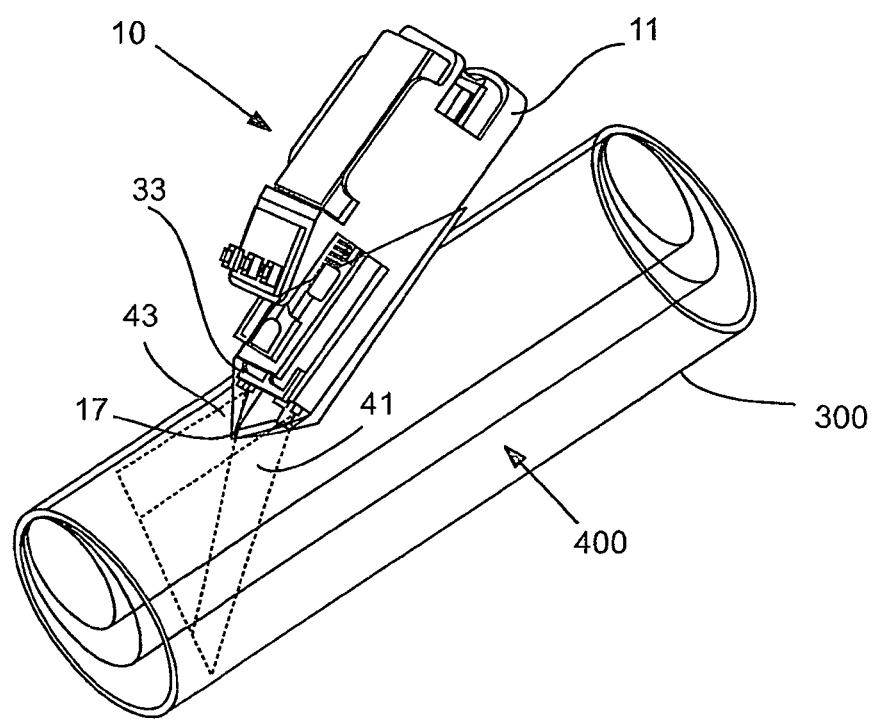
FIG. 15 shows a three-dimensional view of the apparatus of FIG. 5, which is oriented in order to allow the laser beams to be aligned with a structural feature present in a core (with various core diameters being illustrated)

The point 17 also functions as contact portion for contacting the outer surface 400 of the core 300 while moving the body 11 angularly with respect to the core axis to align the body with a plane transverse to the core axis, as best seen in FIG. 15. With this arrangement, the contact portion may provide a reference point on the outer surface 400 at which the indication of the angular disposition of the plane is obtained. Further, the contact portion may function to stabilise the body 11 with respect to the core 300 as it is moved angularly with respect to the core axis. In effect, the point 17 provides a fulcrum about which the body 11 is rotatable (movable angularly) for varying the angular disposition of the body, thereby changing the attitude of the apparatus 10 relative to the core axis.

Figure 4:
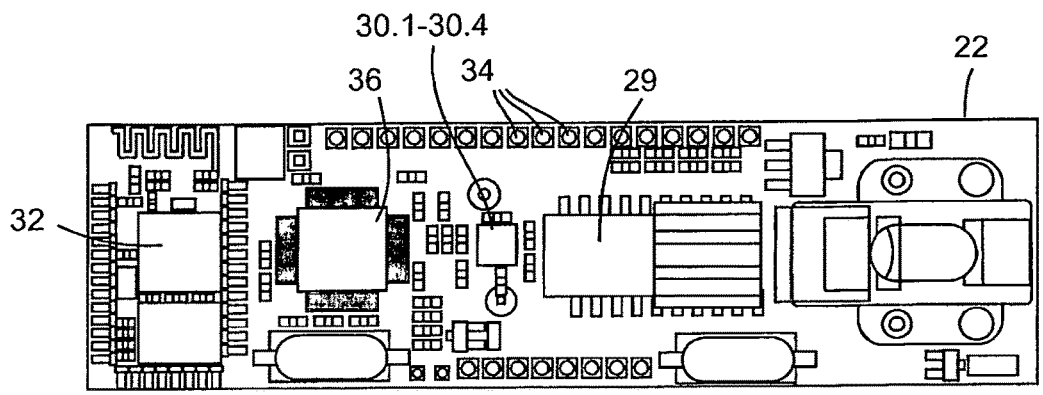
FIG. 4 shows a top, plan view of a circuit board of the apparatus of FIG. 1.

The PCB 22 includes an optical sensor 29, a gyroscope 30.1, an accelerometer 30.2, a compass 30.3, an optional magnetometer 30.4, a Bluetooth communication arrangement 32 (e.g. a Bluetooth radio with an antenna) and a microprocessor 36 (see FIG. 4). This provides the orientation arrangement in this embodiment The PCB 22 further includes a series of pins 34 which can be connected to a GPS unit (e.g. to allow the apparatus 10 to be used as a surface mapping tool). The gyroscope 30.1, accelerometer 30.2, compass 30.3 and magnetometer 30.4 may typically be incorporated into one chip (e.g. a motion-sensing chip). The orientation of the apparatus 10 can therefore be extracted from the chip by using either euler angles or quaternions. This may be done using averaging techniques or Kalman filter methods.

Figure 2:
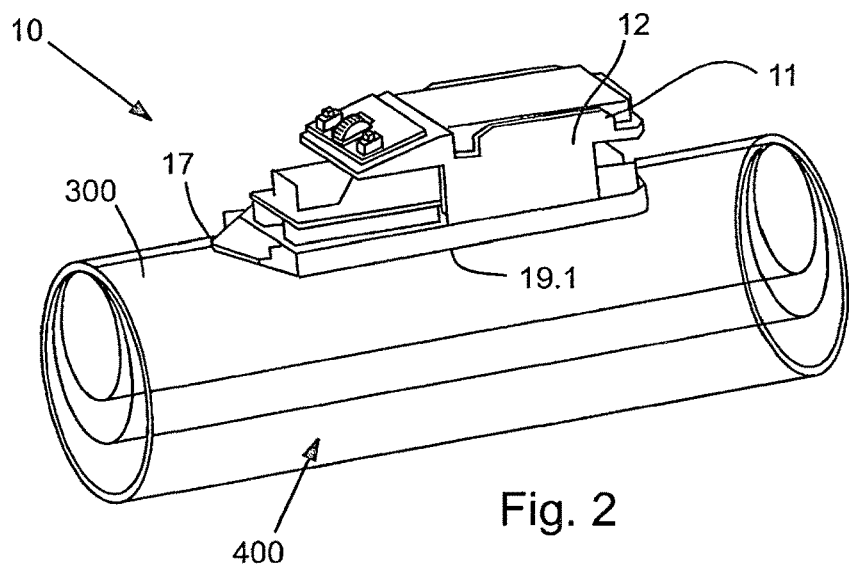
FIG. 2 shows a three-dimensional view of the apparatus of FIG. 1, when positioned along the orientation line on borehole cores with different diameters.

The optical sensor 29 is mounted such that it extends operatively downwardly from a bottom surface of the lower part 26, as best seen in FIG. 9, and is configured to measure the distance which the apparatus 10 travels along the surface 400, say between two measurement points, when the apparatus 10 is placed against and slid/moved there along (in a similar fashion to a computer mouse). In this embodiment, the optical sensor 29 is typically configured to determine relative motion/displacement within an accuracy of about 2 mm. In use, the apparatus 10 would be so positioned on the outer surface 400 of the core 300 in the manner shown in FIG. 2, with the point 17 so positioned as to be in registration with one of two intended measurement points, and data relating to that position captured by way of optical sensor 29. The apparatus 10 would then be moved along the outer surface 400 of the core 300 into a position in registration with the other of two intended measurement points, and data relating to that position captured by way of optical sensor 29. The distance between the two measurement points can then be determined, reflected by the distance over which the optical sensor has moved.

The apparatus 10 further comprises an alignment arrangement which can be used to align the apparatus with a structural feature, when in use. The alignment arrangement comprises an alignment indicator 33. The alignment indicator 33 presents a reference for aligning the body with a plane transverse to the core axis, whereby an indication of the angular disposition of the plane can be obtained by a determination of the attitude (angular position or orientation) of the body 11 relative to the core axis. The plane of interest transverse to the core axis typically comprises a plane represented by a surface of a feature present in the core 300; for example, a plane corresponding to where a planar structure outcrops on the core surface 400. The gyroscope 30.1 and/or accelerometer 30.2 can be in order to determine/measure the orientation of the apparatus 10 once it has been aligned with a structural feature 600 by using the alignment indicator 33, as shown in FIG. 15.

Figures 5, 6, 7:
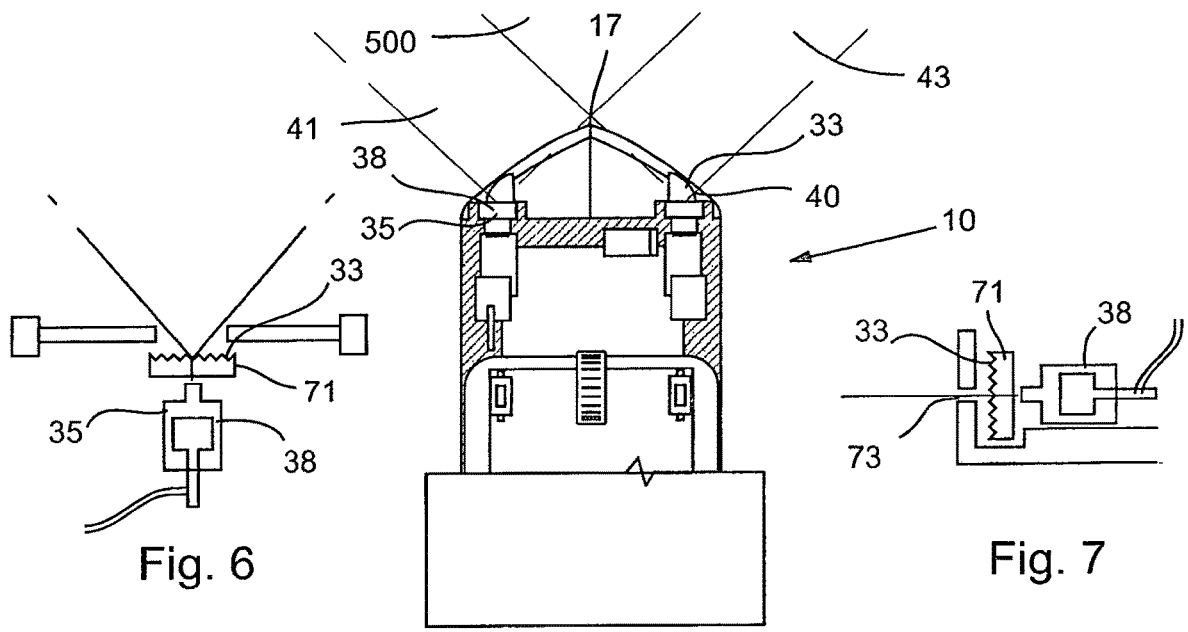
FIG. 5 shows a top view of part of the apparatus of FIG. 1, where two diodes of the apparatus each emit a laser beam that passes through the dispersion lens and then thru a narrow slit in the housing that restricts width of the beam.
FIG. 6 shows a schematic plan view of the arrangement for emitting the laser beam as depicted in FIG. 5.
FIG. 7 shows a schematic side view of the arrangement for emitting the laser beam as depicted in FIG. 5.
Figure 8:
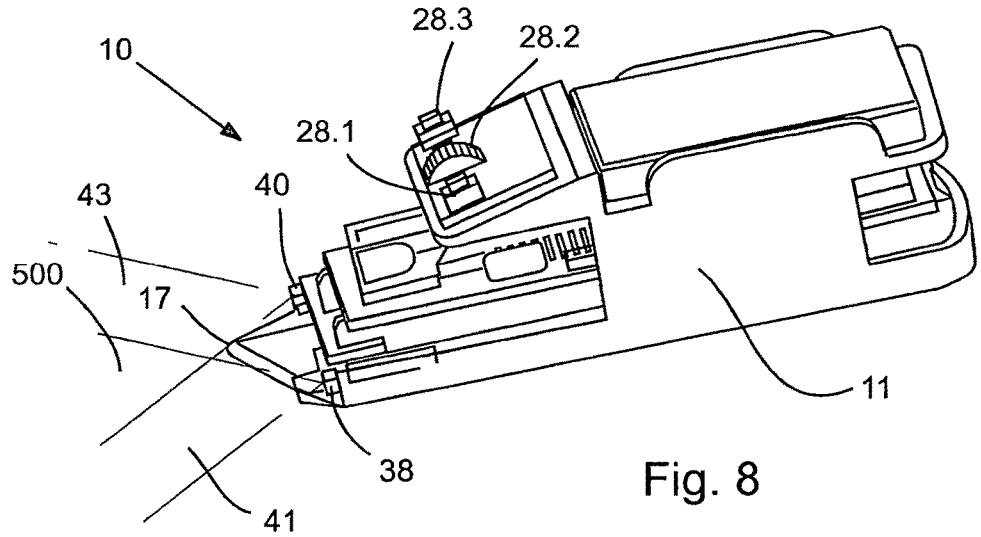
FIG. 8 shows a three-dimensional view of the apparatus of FIG. 5; showing the twin laser beam aligned with a cursor/point of the apparatus and the reference surfaces.

In this embodiment, the alignment indicator 33 is operable to provide visual indication on the surface of the core sample. In the arrangement shown, the alignment indicator 33 comprises a beam-forming arrangement 35 which is configured to emit at least one beam, when in use, which can be used to align the apparatus 10 with the structural feature. The beam-forming arrangement 35 may be configured to emit a single beam or two beams. The, or each of the, beams may be a light beam. The light beam may more specifically be a laser beam. In this embodiment, the beam-forming arrangement 35 comprises two line laser diodes 38, 40 are mounted on respective sides of a front part of the base 16 and are directed forwardly (see FIG. 5). A dispersion lens 71 is mounted in front of each diode 38, 40 in order to allow the diode 38, 40 to emit a 60° beam of light 41, 43, with each beam being aligned with the pointer 17 (see also FIGS. 6 and 7). The base 16 defines a narrow slit 73 which allows the beams to together project a straight line onto the outer surface 400, when the diodes 38, 40 are oriented perpendicularly thereto. If the diodes 38, 40 are oriented at an acute angle relative to the outer surface 400, then, instead of a straight line, an ellipse shape may be projected onto the surface 400. The line/ellipse shape can then be used to align the apparatus 10 with a structural feature exposed on the outer surface 400 of a borehole core 300.

Figure 17:
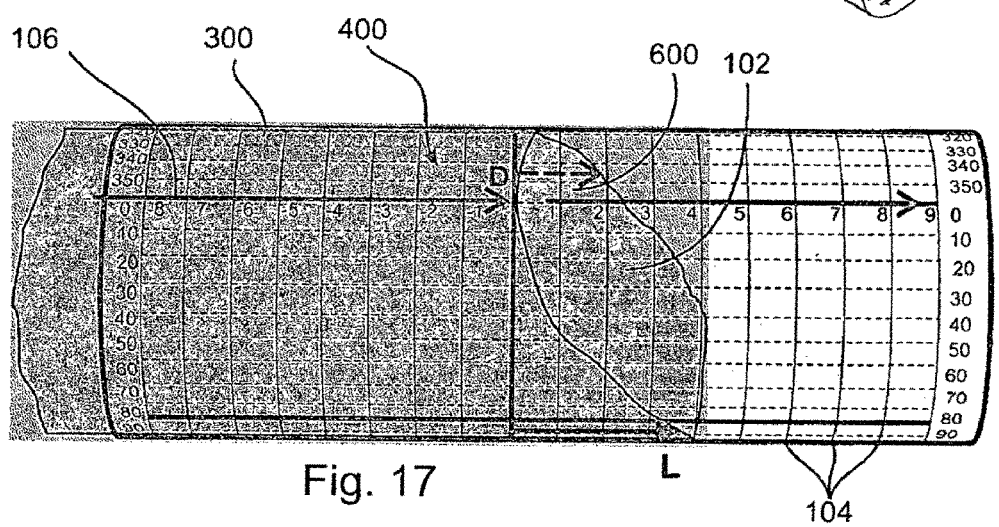
FIG. 17 shows a side view of the arrangement depicted in FIG. 16.

The plane (generally indicated by reference numeral 500) defined by the laser beams 41, 43 can typically be determined by the vector which is at right angles (normal) to the plane. The 60° beams of light 41, 43 are typically designed to provide maximum coverage of the surface 400 of a core 300 in order to help allow accurate recording of a structural feature 600 (see FIGS. 17 and 18), irrespective of the angle of the structural feature 600 in relation to the core 300. The coverage generally ranges from about 52% for a B core (36.5 mm diameter) to about 44% for an H core (63.5 mm diameter).

An LED screen (not shown) is secured to the inner casing 12, above the battery pack 20. The LED screen is operatively connected to the Bluetooth communication arrangement 32 in order to allow a user to communicate with a computer 200 or tablet 202 which forms part of the system 100. The LED screen can, for instance, be used to input parameters such as the depth and structure name (e.g. a planar or linear structure).

The battery pack 20 can, for example, be a rechargeable NiCad battery pack which can provide about 6 hours of continuous use.

Figure 16:
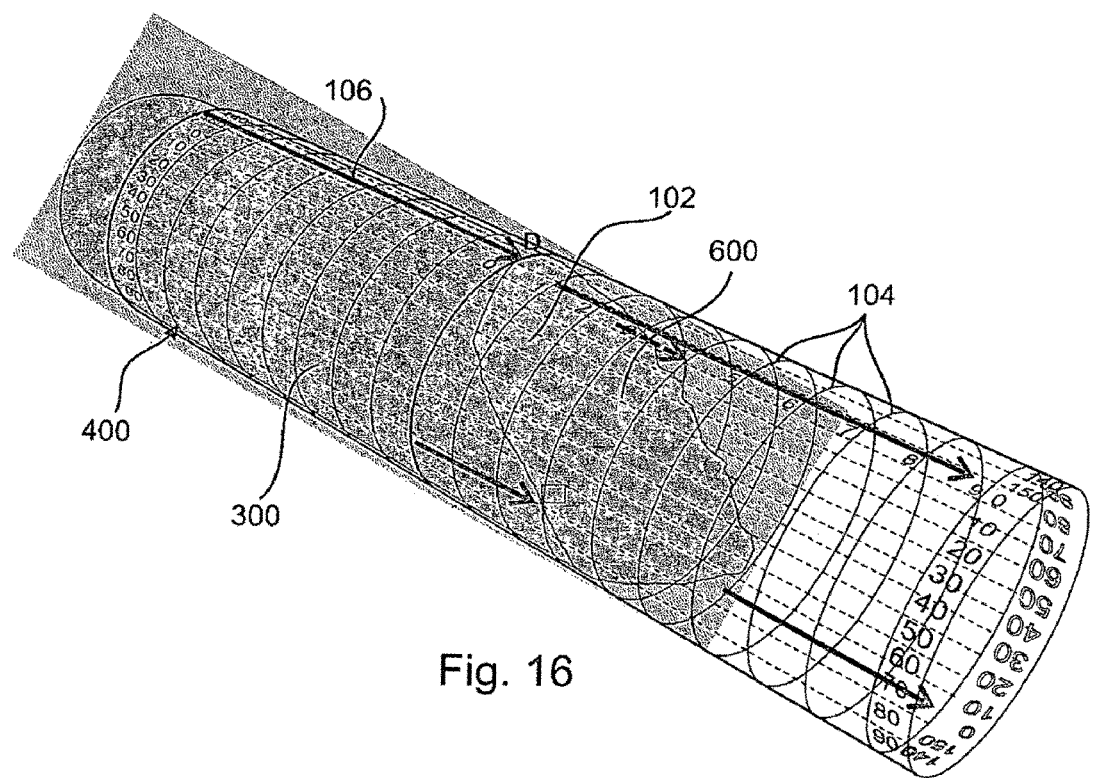
FIG. 16 show a three-dimensional view of a borehole core and indicates possible recording positions to obtain accurate information when recording a planar structural feature.

The capture and recording of data by way of the data-capturing arrangement is initiated through operation of the actuation means 28. In this embodiment, the actuation means 28 comprises one or more operating buttons. In the arrangement shown, there are three operating buttons 28.1-28.3. The button 28.1 is a referencing button which is configured to capture a reference orientation of the apparatus 10 when it is placed against an outer surface 400 and oriented along a bottom-of-core ("BOC") line 106 (see FIGS. 16, 17 and 18) which extends along the length of the core 300. A BOC line is a term that is well known in the industry and will therefore not be described in more detail. The button 28.3 is a record button which can be used to capture a reading, or a number of readings, when the apparatus 10 is aligned with a structural feature 600. The button 28.2 a multifunctional button in that it has a scroll function, as well as a single-click and a double-click function.

By using the single-click function, the computer 200 is instructed to compute a best-fit orientation of a particular structural feature 600 relative to the borehole core 300 temporally. The computation includes determining a dip, dip direction and strike for planar features or a plunge and direction for linear features. It then plots the structural feature 600 as a flashing point on a stereographic projection and as a plate or line on orthographic projection as well as calculate an apparent dip on a prescribed bearing. The orthographic projection is a representation in three dimensions of the borehole, together with the planar and linear structural features 600. A linear structural feature or lineation can be represented as a cylinder with an arrow indicating the direction of movement on the slip surface.

By using the double-click function, the computer 200 is instructed to calculate and save a number of parameters relating to the borehole and the structural feature. The computer 200 then saves the data, once a datum has been verified and saves the geometric disposition to a data spread sheet. The calculated parameters may include (but is not limited to):

down-hole depth (m) to where a mid-point of a structural feature 600 intersects a center of the core 300.
borehole orientation: The azimuth and inclination of the borehole at that depth.
borehole co-ordinates (e.g. x, y and z coordinates) and vertical depth to the structure or geological contact.
real space orientation of the planar structure (e.g. the dip and dip direction)
alpha, beta and gamma angles of a structure used in the existing Internal Core Angles method of determining the orientation. The alpha angle refers to the angle between a vector pointing along the length of the core 300 and the plane in which the planar feature extends.
apparent dip or pitch of a structure in a predefined section line.

Typical data which is sent to the computer for further processing includes:
Quaternion data: The orientation of the apparatus 10 is sent through as a unit quaternion.
Acceleration data: The raw acceleration data, in the three dimensional directions (x, y and x), is sent as a fraction of gravitational force (g).
Gyroscope data: Data on the raw rotation around the three axes (x, y and z).
Optical sensor data: The movement of the optical sensor in two directions (in meters).
Optical sensor status: The sensor identity, quality and status.
The status as to whether any of the buttons have been pressed.
Magnetic field The apparatus 10 can be used in two different ways in order to measure the orientation of structural features 600 in a core 300.

The first method is referred to as the alignment method. This method offers a process of acquiring large structural data sets, primarily for stereographic analysis where the precise depth is not critical or even required. An example would be measuring the bedding planes to determine the direction of folding or measuring fore sets to determine the current direction or direction of flow. The process involves aligning the unit using a flat laser beam or the base of the device 10 with the structure.

The normal method involves aligning the apparatus 10 with the structure 600 using either the base or the planar laser beam 500 and acquiring at least four recordings off the surface 400 of the planar structure 600. The program statistically analyses the recorded measurements and calculates the 'plane of best fit' and determines the 'margin of error'.

The method also offers a quick procedure that facilitates the rapid acquisition of data directly from the core 300 in a core tray. The program only requires one alignment reading per structure 600 before checking and saving. The alignment method utilises the gyroscope 30.1 and accelerometer 30.2 in order to determine/measure the orientation of the apparatus 10 once it has been aligned with a structural feature 600 by using the laser beams 41, 43. Alternatively, the edges 19.1, 19.2 of the lateral sides of the base 16 can be aligned with exposed structures (the alignment process will be described in more detail below). This method is convenient in gathering large data sets for stereographic analysis in situations where the exact depth of the structural feature 600 is irrelevant. Routine measuring of structural feature 600, particularly planar features such as beddings, foliations, fractures, faults, etc., can be undertaken by utilizing the laser beams 41, 43 when the core 300 (more specifically a sample of the core 300 taken from a borehole) is positioned in a core tray. A technician should typically ensure that the core samples are properly pieced together and that the BOC line 106 is correctly aligned in the tray. Drill breaks and orientation discontinuities should be clearly demarcated as these may have a detrimental effect on the measurement of the structural feature 600.

Figure 19:
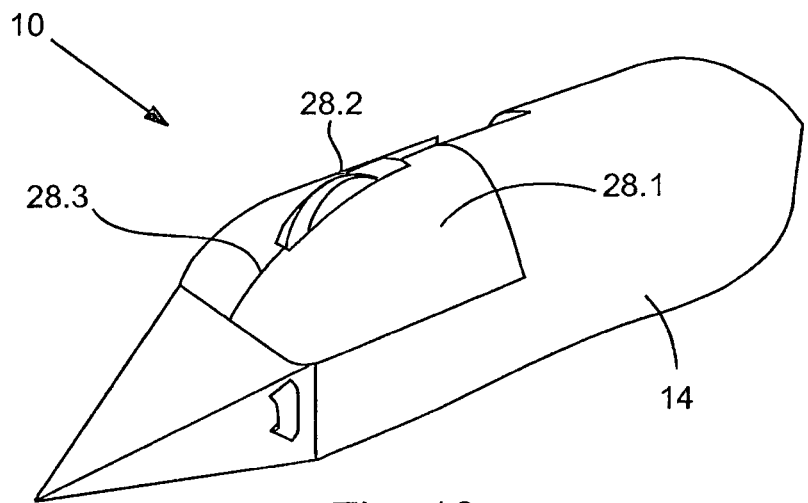
FIG. 19 shows a three-dimensional view of the apparatus of FIG. 1, with a possible outer casing.

The second method is referred to as the dimension method which uses the optical sensor 29 and the gyroscope 30.1 to measure a down-hole depth of the apparatus 10 and to determine the angular displacement thereof, on the surface 400. This method is generally preferred when the accurate depth or precise geometric disposition/orientation of a structural feature 600, such as a major fault or fold axis, is critical. Detailed and accurate structural measurements, in particular the recording of linear features such as slickenside striae, rodding, boudins, or fold axes, may require the core 400 to be removed from the core tray and placed in a small V-bench to allow the apparatus 10 to be moved over the outer surface 400 of the core 300. To start recording, the apparatus 10 is referenced to a depth mark line (see reference numeral 104 in FIGS. 17 and 19) parallel to the BOC orientation, i.e. by using the button 28.1. By simply sliding the apparatus 10 over the outer surface 400 of the core 300 and aligning the point 17 with the position where the structural feature 600 intersects the outer surface 400 and recording several readings on the same feature 600, the apparatus 10, together with the computer 200, can determine an estimated orientation/disposition of the feature 600 in relation to the core 300.

A plane can be fitted in three dimensions, once three or more points on the plane are known.

Since the surface 400 of the core 300 forms a cylinder, if the displacement along the length of the core 300 can be kept separate from the displacement along/around the circumference thereof, the position/location of a particular point can be obtained. Once three or more points are measured in this way, relative to a fixed reference point on the orientation line 106, the orientation of a plane relative to the core 300 can be calculated. If more than three points are available, a plane of best fit can be derived. A linear feature can be derived by using two known points at which the lineation intersects the surface 400. If these points are measured repeatedly, the line of best fit can be derived and the margin of error is calculated.

The innate remnant magnetic disposition displayed by the core 300 can be determined by using the magnetometer 30.4. Measuring the direction of the remnant magnetism of individual core samples from the same core 300 could be useful in orientating/aligning the core samples correctly, such that the orientation line 106 extends across drill breaks (i.e. the direction of the remnant magnetism for the core samples should typically be in the same direction).

When the earth's magnetic field is subtracted and the residual field measured in proximity to the core 300 is correlated with the orientation, the magnetisation of the core 300 can be extracted as a function of depth.

All the data derived/calculated by the apparatus 10 is sent to the computer 200 (or tablet 202) via the Bluetooth communication arrangement 32 for further processing. Specialised software is installed on the computer 200 (or similar communications enabled computing device) in order to provide a user with purposeful visual feedback of the structures 600 logged by the apparatus 10 on a computer (or other display) screen.

The software typically integrates data received from various sources, and processes and combines the data with the structural feature data (received from the apparatus 10). Down-the-hole survey data, geological borehole logs, geotechnical and structural data are imported into the software by using Excel spreadsheets. The data is then processed, amalgamated with the structural feature data and can be exported in spreadsheet or text format into geological processing or mine planning software programs. One of the unique attributes of the software is the ability to depict planar structural features as planes plotted within the borehole in three-dimensional orthographic projection (this will be described in more detail below).

The software utilises a vector model to derive borehole coordinates in three dimensions and determine the plane geometry of a structural feature 600. The apparatus 10, together with the software, has the ability to measure and calculate the orientation of structures accurately (even at relatively high core (Alpha and Beta) angles), and to record the orientation of non-penetrative linear structural features, such as fold axes, crenulations. The software can provide a user with a three-dimensional orientation of the borehole and structural feature 600 immediately (in real-time) at the time of logging (as soon as the necessary processing has been done as mentioned above). The orientation may be displayed in orthographic and stereographic projection, thereby allowing a user to audit and verify the datum prior to saving.

The operational procedure involves; initially referencing the apparatus 10 relative to the core 300 and BOC line 106 and then measuring the orientation of the structural feature 600 by either aligning the apparatus 10 with the structural feature 600 or by moving the apparatus 10 over the surface 400 and locating several points where the structural feature 600 intersects the surface 400 by aligning the point 17 therewith. Accurate measurements of a structural feature 600 can be obtained by recording several measurements of the feature 600 on the surface 400. The software then statistically analyses the data received from the apparatus 10 and produces a best-fit estimation of the orientation of the structural feature. This feature of the software can also be used to analyse the orientation of the same repetitive feature 400, such as bedding or fore sets, to calculate the best fit or average orientation of the measured structural feature 600.

The software includes various software modules which are described here below:

Survey Module

Down-the-hole survey data can be entered manually on the computer in a single shot survey, or imported from any multi-shot survey tool. Once the data is entered, the coordinates are calculated and the projection of the borehole can immediately be viewed as a three-dimensional orthographic projection on a display screen. By amending the borehole azimuth and inclination cells, the software automatically recalculates the down hole coordinates and amends the borehole three-dimensional plot accordingly. The software allows a user to zoom in and out, scroll up and down the borehole, and to freehand pan and rotate the view angle.

Geology Module

Existing borehole logs, together with the structural feature data received from the apparatus 10, can be imported into certain software parameters, such as depth, lithological unit, description and a unique identifiable colour which can be imported directly from an Excel spreadsheet, as would be understood by a person skilled in the art.

Stereographic Projection Module

Figure 10:
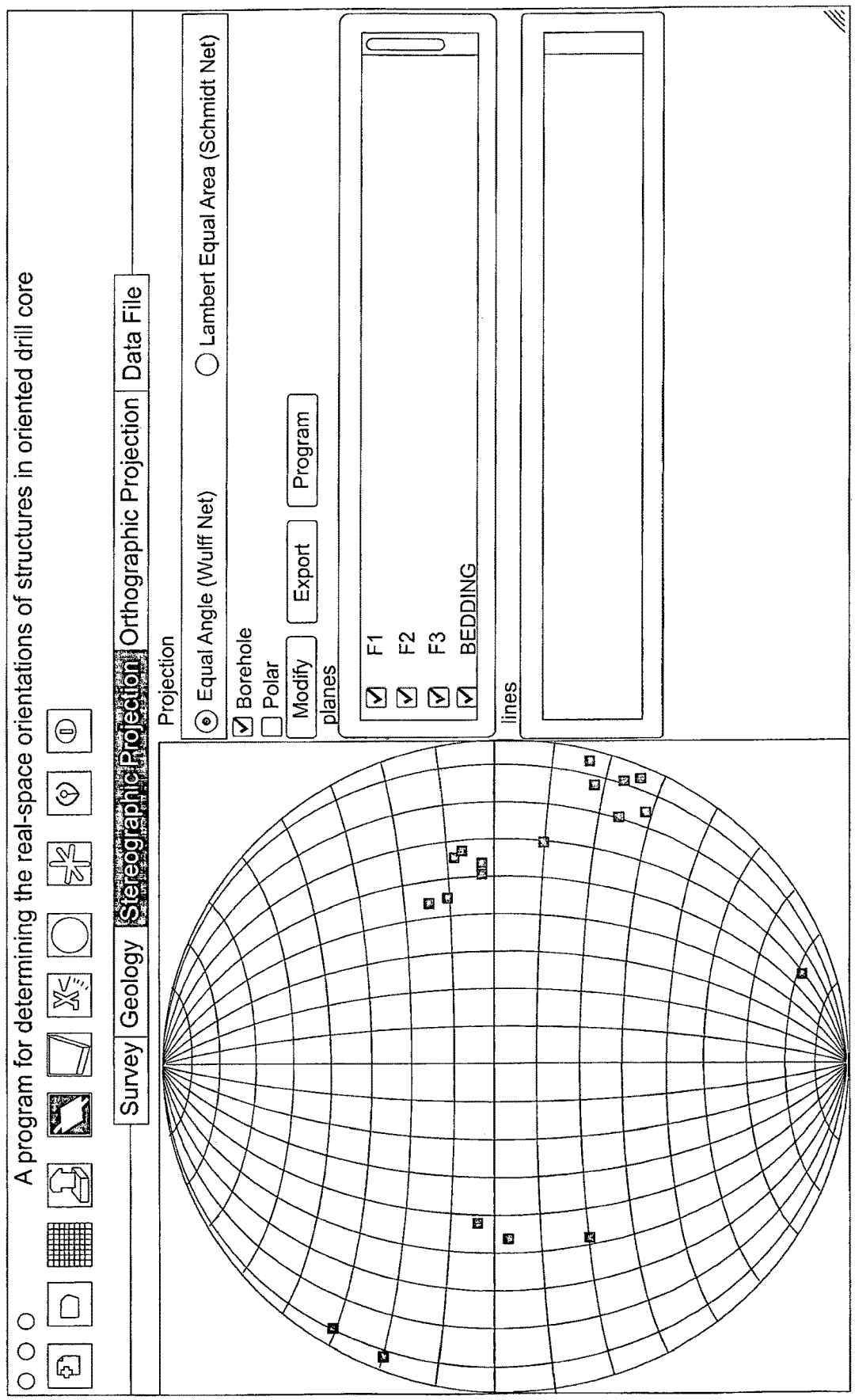
FIG. 10 shows a typical example of a stereographic projection displaying data collected by the system.

The orientation of structural features 400 is automatically plotted by the software in stereographic projection, with various options available. Each type of structure is displayed in a unique colour for easy identification and a user/technician has the option to display specific structure types selectively. The data can be exported to recognized structural analytical programs. In this regard please see FIG. 10.

Orthographic Projection Module

Figure 11:
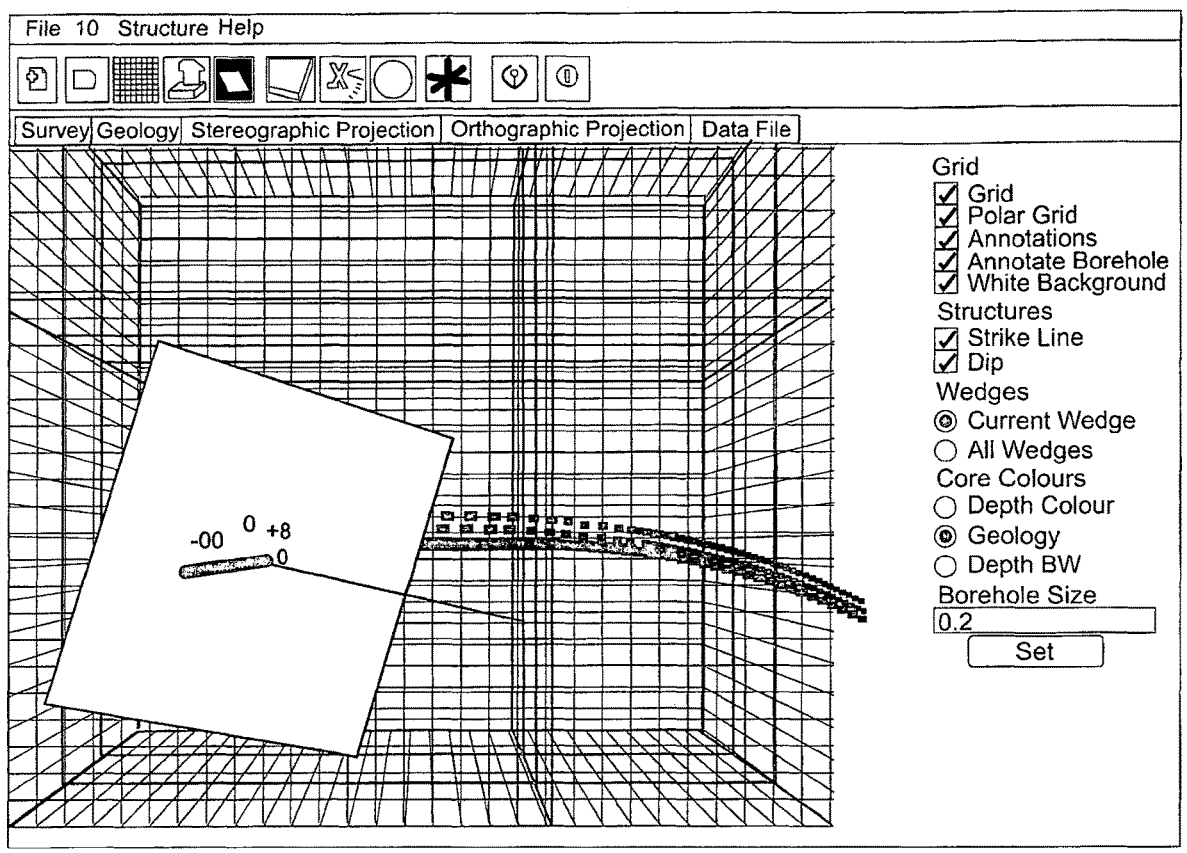
FIG. 11 shows a typical 3-dimensional orthographic projection of a borehole plot displaying an extended planar structure
Figure 12:
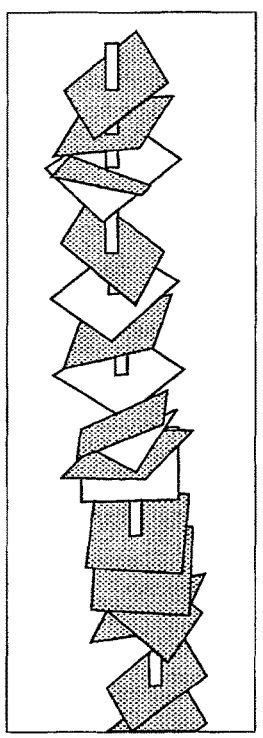
FIG. 12 shows a three-dimensional orthographic projection displaying the various structures plotted as plates, showing the strike and dip (with the borehole typically shown in colour coded geology)
Figure 13:
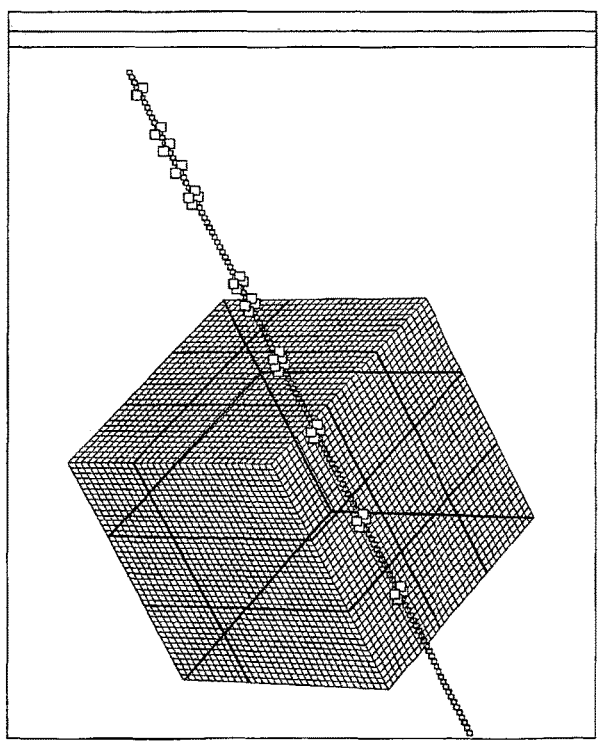
FIG. 13 shows a typical zoomed out plot of the borehole with a reference grid.

Referring now to FIGS. 11-13, the orientation of a structural feature 400 is also automatically determined and plotted to a three-dimensional orthographic projection. Planar structures, with lines depicting strike and dip direction are projected as rectangular plates on the planar surface. Linear features, displayed as small rods and structures, such as faults where the direction of movement could be determined, are plotted as arrows showing the orientation and direction of movement. The software allows a user to zoom in/out, scroll up and down the borehole and to freehand change and rotate the view angle. The background can be annotated with various grid overlays, including a coordinated orthographic three-dimensional grid over the borehole projection, or a circular grid with compass bearing and the inclination of the borehole at that depth. Scrolling up and down the borehole changes the position of the grid down the borehole. By scrolling up and down the borehole, the grid can be positioned such that individual structures plots in the centre of the grid, the strike and dip directions and can be physically measured/recorded off the grid if required.

The strike and dip are depicted as white or black lines on the animated plane of the structural feature 600. The software provides an option to change the colour and size of individual structural plots. The ability to increase the size of the plotted planes is useful in extending the size and projecting major structures. These structure planes can be enlarged to provide the user with an idea of where the structure should be running under ground. This model can then be imported directly into a user's mine modelling software where this enlarged structure can be inspected throughout the mining area.

Data File Module

This is a multi-functional module. The primary function is to provide a database for the storage of all the structural feature recordings and calculations. The database can be exported to an Excel file. The secondary function serves to edit and correct individual structural feature records. Certain specific cell values can be amended or changed in order to adjust the calculated results automatically. On saving the input parameters, up to 16 different parameters are calculated and saved to a data file. In this regard, reference is specifically made to FIG. 14.

The following parameters may, for example, be calculated:
  Calculated parameters pertaining to a borehole:
  down-hole depth (in meters) to where a mid-point of the structural feature intersects a center of the core 300.
  borehole orientation, azimuth and inclination at the down-hole depth.
  borehole co-ordinates (x, y, and z) and vertical depth to the structural feature.
  Calculated parameters pertaining to planar features:
  real space orientation of the feature, dip and dip direction.
  alpha and beta angles of the feature used in the Internal Core Angles method of determining the orientation.
  apparent dip of the planar feature in a predefined section line.
  Calculated parameters pertaining to linear features:
  down-hole depth (in meters) to where a mid-point of the linear feature intersects the center of the core.
  orientation represented by the plunge and trend of the linear feature:
    trend—direction in which a linear feature plunges.
    plunge—angle between the lineation and the horizontal.
    pitch of the lineation—being the angle between the feature and a predefined section line.
  gamma and/or delta angles of the structure used in the Internal Core Angles method.
  Misfit—the angular difference between the lineation and a planar feature in which it occurs.

Procedure for Recording Structural Features

Here below follows an example of how a particular structural feature may be recorded by the system 100:
  i. Initiate a new log by clearing existing data in the survey module.
  ii. Import down-the-hole survey data into the survey module. Should the actual down-the-hole survey data not be available, then the borehole depth and the initial estimated borehole survey, azimuth and inclination can be inserted manually by using the computer 200. The actual borehole survey can be imported at a later stage and the orientation of all the structural recordings will then be automatically adjusted/amended. The geometric disposition/orientation of structures is computed relative to the borehole survey.
  iii. In order to capture structural feature data, an "input structure" screen is opened by selecting the appropriate option at the top of a user interface screen on the computer 200.

Input Structure Screen

The input structure screen displays a number of cells which allows a user to enter information regarding the borehole/borehole core.

A visual orthographic 3D projection of the orientation of the apparatus 10 relative to the core 300 is displayed. The display provides an indication that the apparatus 10 is working properly and is connected wirelessly to the computer 200.

The following information may, for example, be entered by a user:
  The downhole depth to the recording. The depth may be inserted manually on the computer or inserted using the scroll function of the button 28.2 on the apparatus. The options may be a planar structure, linear structure or a combination thereof.
  The technique/method used to record the structure. The options may be:
    i. The alignment method; or
    ii. The dimension method.
  These two methods will be described in more detail below.
  A unique name to identify the structure.
  Margin of Error: This allows a user to define an acceptable margin of error level.
  iv. Insert the borehole details:
    Units of measure (either metric or Imperial).
    Core diameter (the most common core sizes are displayed in a drop-down menu on the user interface).
    Top- or Bottom-Of-Core orientation.
  v. In a depth field), insert the down-hole depth at which the apparatus 10 is referenced.\
  vi. Method: Select the routine used to record the structural feature 600:
    The program statistically determines the Plane of Best Fit (PBF) and calculates the margin of error for a desired degree of confidence, thereby determining the number of readings to be taken on a single structure.
    The program determines the offset distances on the left and right-hand side of the core 300 from the position where the trace of the structural feature intersects the orientation line. This enables the user to verify and check the validity of the recording.
    The program determines the real space geometric orientation of the planar structure, i.e. the dip and dip direction, and the plunge and plunge direction for linear structures in relation to the orientation line.

The geometric disposition of the orientation line is derived from the data imported into the survey module.

The margin of error is determined by the irregularity of the structure and the accuracy/precision of the measurement recordings.

The program utilizes the collar coordinates, x, y, and z together with the down-hole survey data to determine the geometric orientation and coordinates of the mid point where the structural element intersects the middle of the core.

Alignment Method

This is a relatively quick and easy method of measuring structures in core samples by simply aligning the apparatus with the structure.

The apparatus 10 is firstly referenced along the orientation line 106 and then moved in order to align the apparatus 10 with the structural feature 600. The apparatus 10 can be aligned by using either the laser beams 41, 43 or the edges 19.1, 19.2 of the lateral sides of the base 16. This method is a rapid data acquisition method to collate structural data for stereographic analysis. Multiple structures can be recorded from a single reference.

Figure 22:
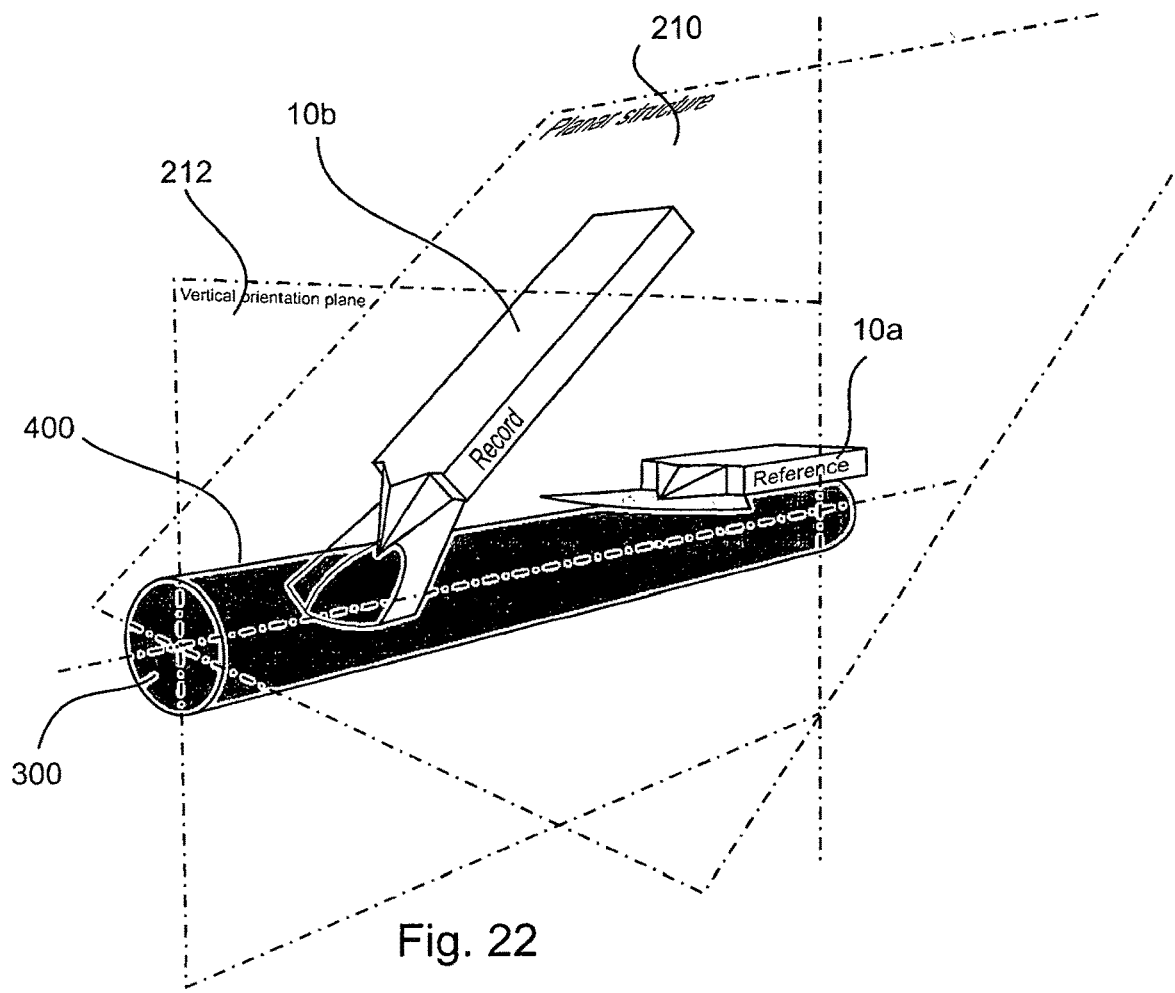
FIG. 22 shows a three-dimensional simulation of how an apparatus, in accordance with the invention, can be used to capture a planar structural feature using a quick alignment method.

Planar structures: Either the base 16 of the apparatus 10, or the laser beams 41, 43 can be used to align the apparatus 10 with the structural feature 600, depending on whether the structure 600 is exposed on the outer surface 400 of the core 300. FIG. 22 show an example of how an apparatus 10 can be first be referenced (see reference numeral 10a) and thereafter be oriented such that the laser beams 41, 43 project along a surface of a planar feature (i.e. to align the beams 41, 43 with the surface), to thereby align the apparatus 10 therewith (see reference numeral 10b). By clicking the record button 28.3, the orientation of the feature 600 is measured. By single clicking the button 28.2, the computer 200 temporarily determines the orientation of the feature 600 and plots the feature 600 as a flashing (blinking) point on a stereogram and a three-dimensional orthographic projection. Once the results have been validated, it can be saved on a database by double clicking the button 28.2. In certain circumstances, more accurate results can be obtained by taking several readings by aligning the apparatus 10 at varying positions on the feature 600, before clicking the button 28.2.

The procedure for recording unexposed planar structures using the Alignment method may be summarised as follows:

The apparatus 10 is initially referenced by placing it with the point 17 positioned anywhere on the core 300 where the vertical orientation plane intersects the surface 400 of the core 300. The reference button is then depressed to initialize the registration. The laser beam/diodes 38, 40 turns on automatically once the alignment method is selected and the apparatus 10 can then be lifted off the core surface 400.

The point 17 is then positioned at any point where the trace of the planar structure 600 outcrops on the core surface 400. By turning and lifting the apparatus the laser beams 41, 43 can be aligned with the outcrop of the structure 600 on the core surface 400. The record button 28.1 is then depressed. Any number of recordings can be taken along the outcrop of the structure 600 on the core surface 400.

The program determines the accuracy and reliability of the measurements by calculating the mean and standard deviation of the measurement.

Once the operator is satisfied with the reliability and number of recordings a "Check" button is depressed and the orientation of the structure is determined and displayed as a flashing point on the Stereographic projection. When the operator is satisfied with the projection of the structure depressing a "save" button provided on a user interface screen, stores the data to the data file.

Lineation (Linear Inertia): The edges 19.1, 19.2 of the lateral sides of the base 16 can be used to align the apparatus 10 with the micro structural features 600, otherwise the procedure is the same as for the planar structures. It should be noted that only exposed lineations can be measured using this method.

In the procedure for recording linear structures using the Alignment method, the base or the sides of the apparatus can be used to record the orientation of planar or linear elements exposed on surfaces of breaks within the core.

A combination of planar and liner structures can be recorded by combining the procedures set out above.

Dimension Method

Figure 23:
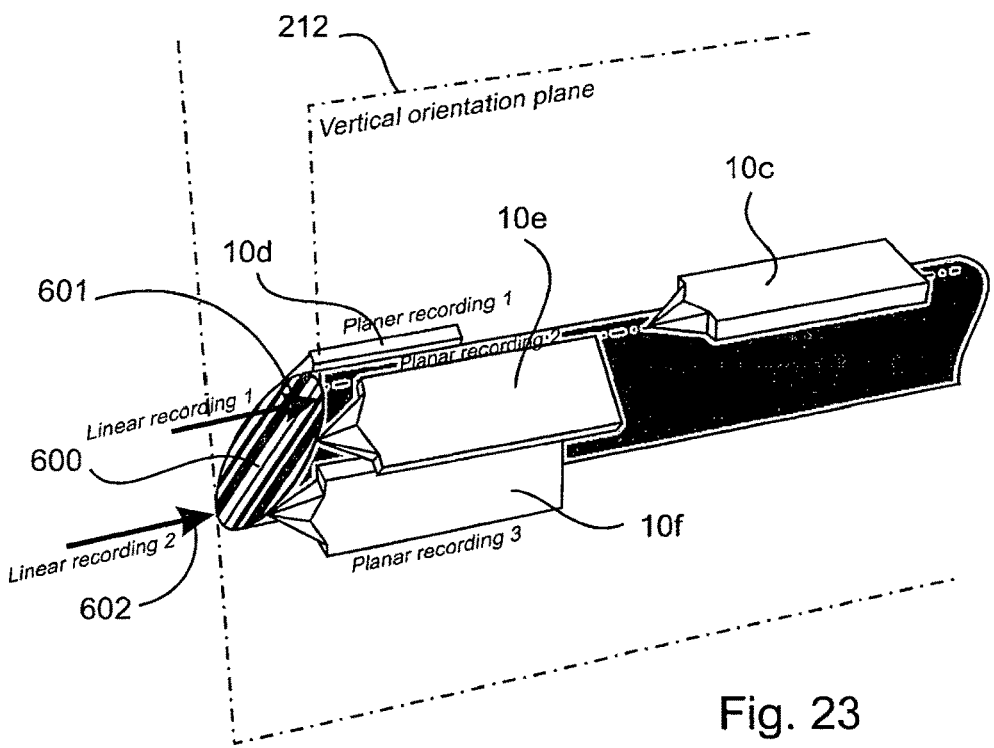
FIG. 23 shows another three-dimensional simulation of how an apparatus, in accordance with the invention, can be used to capture planar and linear structures/features using a dimension method.
Figure 24:
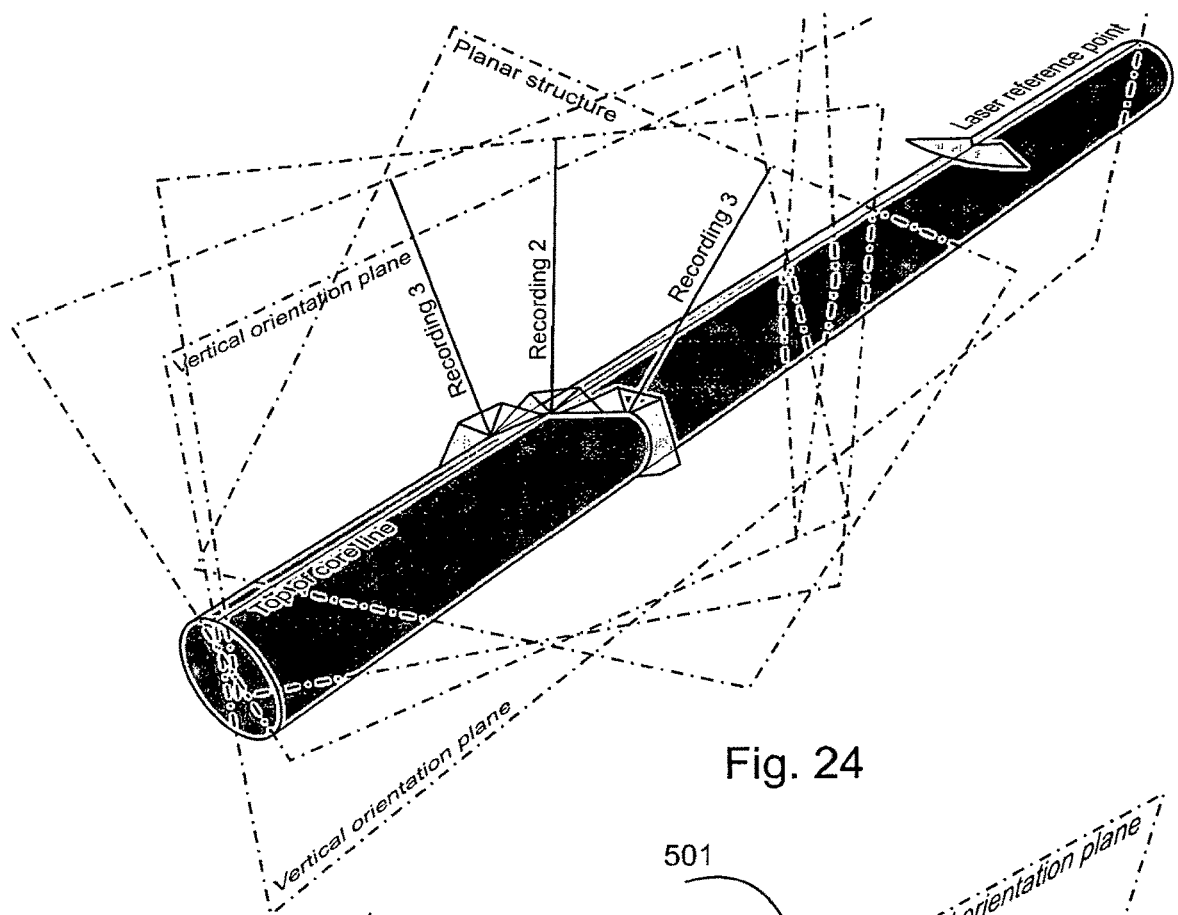
FIG. 24 shows a three-dimensional simulation of how a planar structural feature can be captured using the alignment method using the lasers/diodes to record the orientation of the structure.
Figure 25:
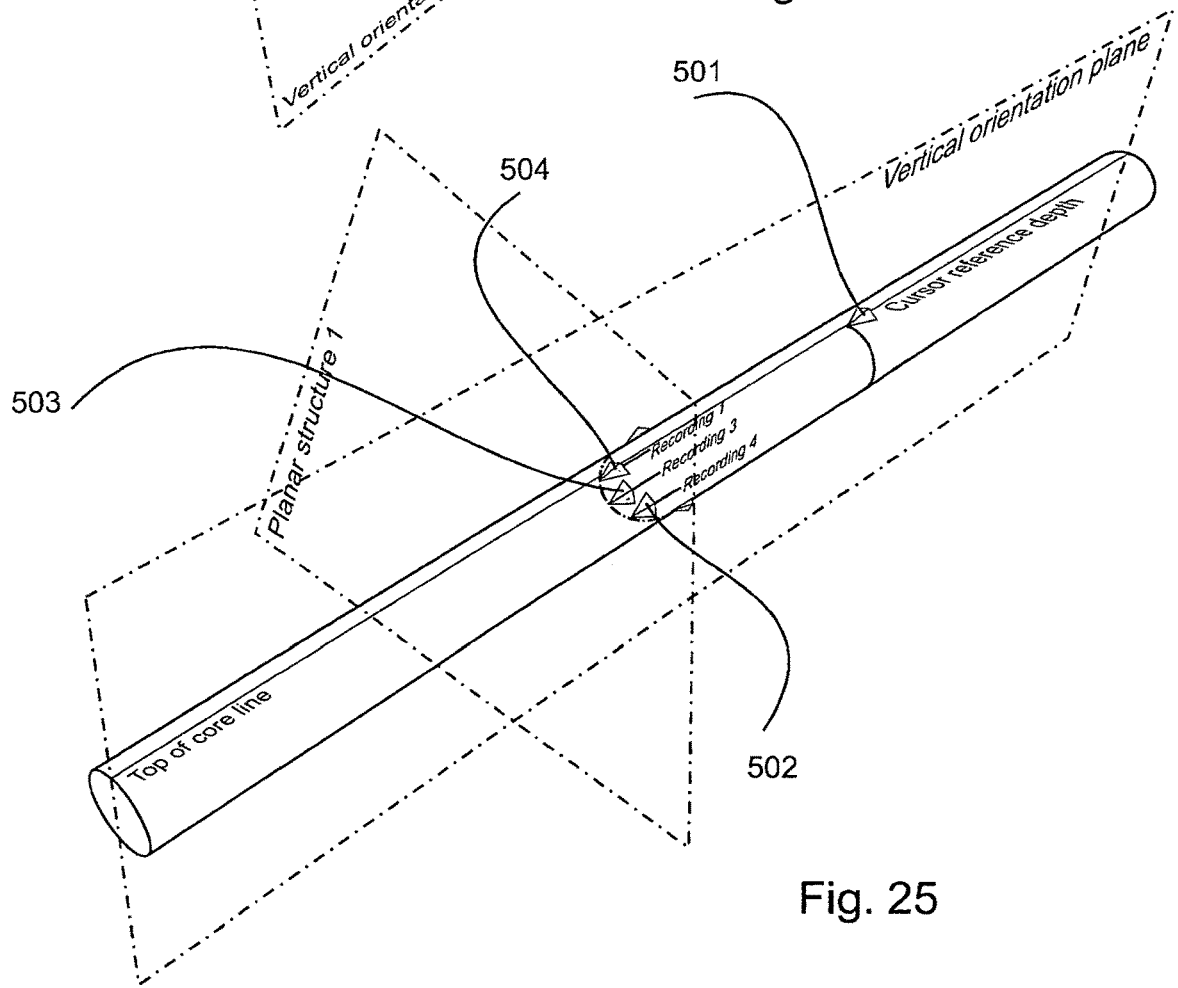
FIG. 25 shows a three-dimensional simulation of how a planar structural feature can be captured using the dimension method to position the apparatus on an outcropping trace of the planar structure on the surface of the core.
Figure 26:
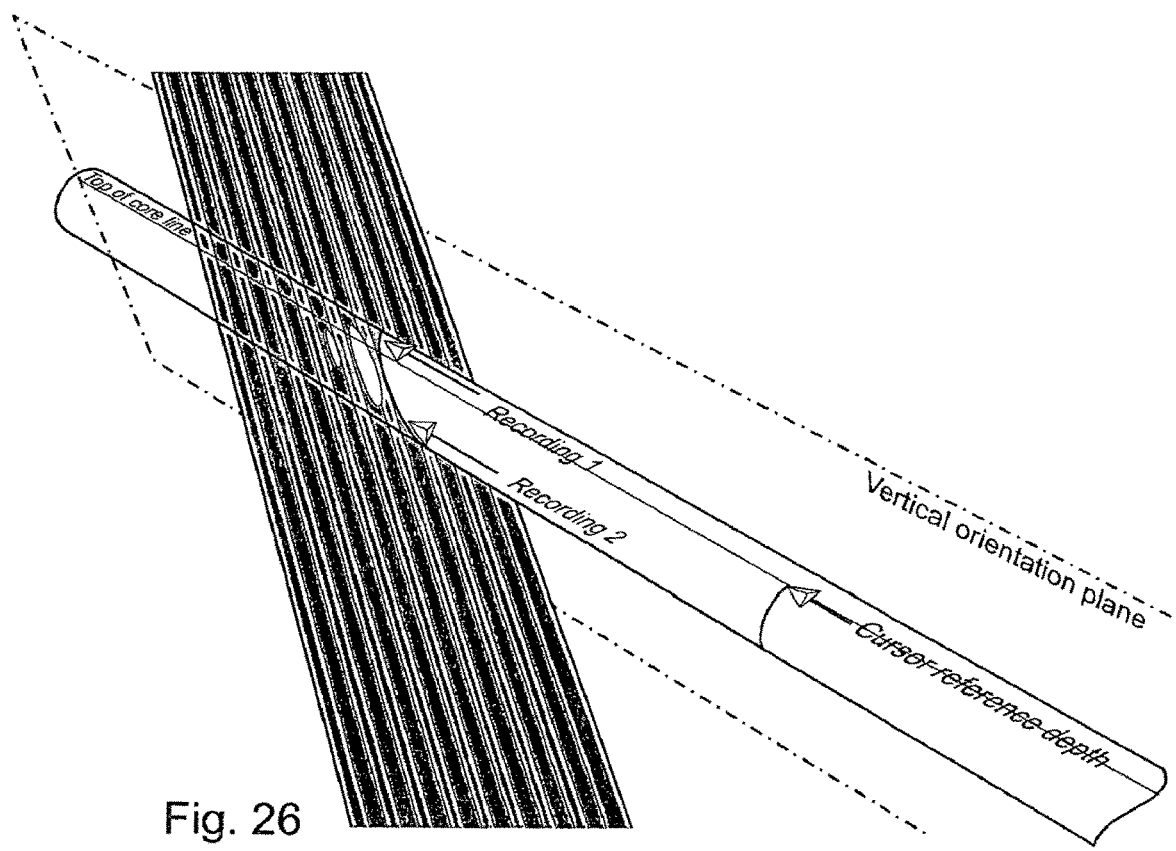
FIG. 26 shows a three-dimensional simulation of how a linear structural feature can be captured using the dimension method to position the apparatus on two positions where a linear feature outcrops on the surface of the core.
Figure 27:
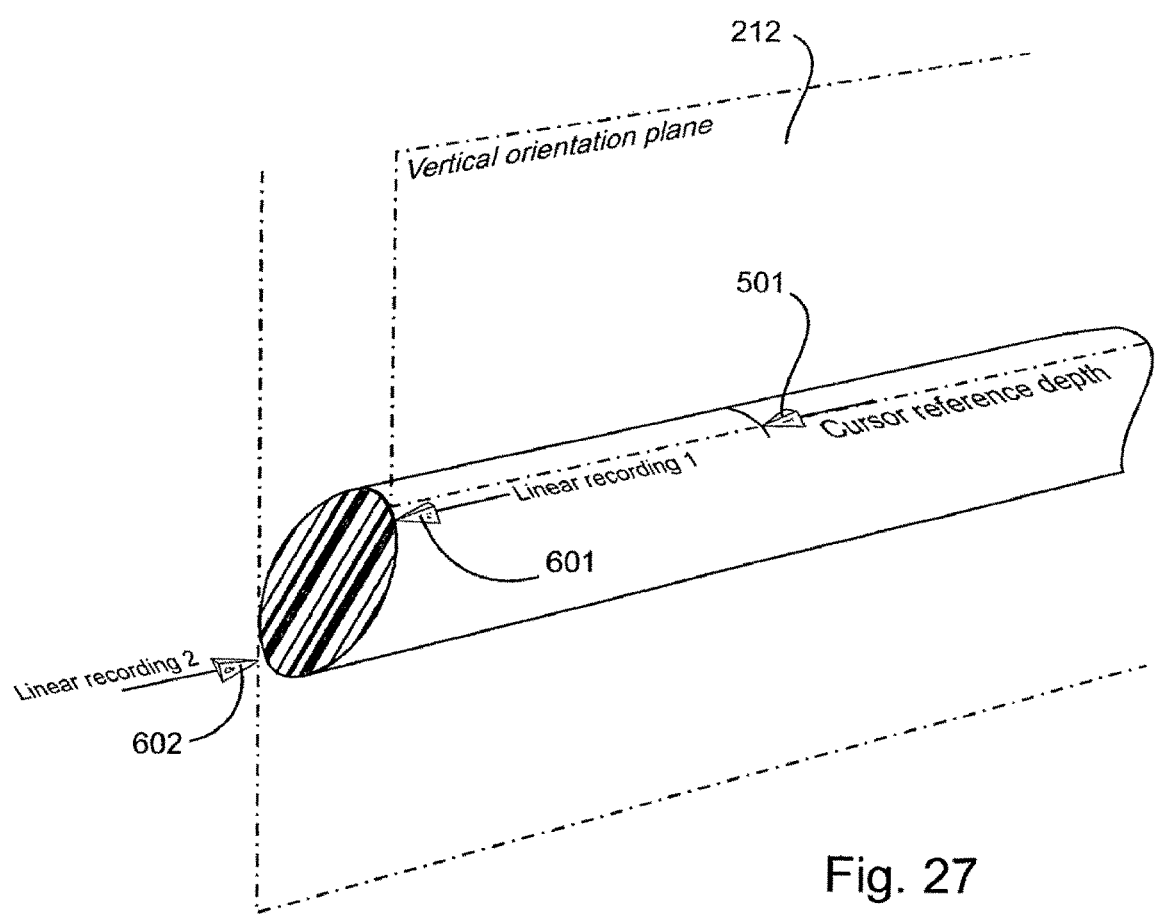
FIG. 27 shows a three-dimensional simulation of how a linear structural feature exposed on a slip surface, such as slickensides on a fault, can be captured using the dimension method to determine the direction of movement on the fault.

The apparatus is firstly/initially referenced at a specific depth along the vertical orientation line 106 (see reference numeral 10c in FIG. 23, as well as FIG. 25 (see specifically the position indicated by reference numeral 501)). The apparatus 10 is then moved in close proximity along the surface 400 to record various positions on the feature 600 exposed on the surface 400 (see reference numerals 10d-f in FIG. 23 which refer to various positions of the apparatus 10 in which recordings can be taken (in addition, also see the positions indicated by reference numerals 502-504 in FIG. 25). Multiple readings are required for an individual structure recording. Planar structures, linear structures, or a combination thereof, can be recorded. For lineations, only two recordings are required to determine the orientation of the structure. In this regard, please see FIGS. 24 and 27 in which reference numerals 601 and 602 refer to two positions where recordings can, for instance, be taken in order to determine the orientation of a lineation.

vii. Define the unique identifying structural feature identification, such as bedding, foliation, cleavage, or F1.

viii. Reference the apparatus 10 by placing it on the core with the point 17 positioned on the BOC line 106. For the quick alignment method: the apparatus 10 only requires to be referenced once if the structural features are recorded in a core tray. For the dimension method, the apparatus 10 should be referenced on the BOC line 106 with the point 17 positioned at a specific depth.

ix. Structure identification: Select a unique name for the structure such as cleavage 1, bedding, F1 fold, etc.

x. Measurements: Each time the record button 28.3 is selected, the software calculates the x, y and z vector values and determines the mean and standard deviation. These values determine the accuracy and reliability of the data.

Operational Procedures

The system 100 uses various techniques for recording the orientation of structural features 400 in cores 300. To undertake a structural analysis of a core 300 and in situations where depth is not an issue, the structural features 600 can be recorded with the core 300 in a core tray. The laser beams 41, 43 can simply be aligned with the outcropping trace of the planar feature on the surface 400. For a more detailed analysis, the core 300 can be placed into a small V-bench and the apparatus 10 can then be moved along the surface 400 and positioned where the structural feature 600 is exposed on the surface 400.

Stereographic Analysis

Sterographic projections can be used to verify and check the integrity of the data prior to saving.

After all the relevant orientation data of the apparatus 10 has been recorded for a particular structure, the data is processed by the computer 200 and plotted stereographically The processed data can also be exported as text or in spreadsheet format into other structural data processing programs.

Orthographic Analysis

Once the borehole survey details have been entered or imported, together with the core size/diameter, the borehole is displayed in three dimensions in the orthographic section. The appropriate tab can then be selected on the interface screen in order to enter a data-capture mode in which the apparatus 10 can be used to capture data on the structural features 600 present in a core 300. The core 300 is typically positioned in a core tray (which should be carefully pieced together in order to ensure accurate results). The logging procedures generally require firstly, for the apparatus 10 to be referenced (at a specific reference point) and orientated relative to the BOC orientation line 106. This is followed by various techniques for recording the structural features 600, be it planar or linear, and then final corroborating by returning the apparatus 10 to the original reference point. This way the device is able to re-calibrate itself and in turn certify and confirm the measurements taken prior to the re-calibration, by going back to a known point. The methods whereby the optical sensor 29 is not used, and reliance is only placed on the gyroscope 30.1 and accelerometer 30.2 to measure the orientation (or direction) of the structural feature 400, are less accurate when compared to using the optical sensor 29 as well. The error in the angle of the structural feature may be up to 5 degrees. The more accurate method requires the apparatus 10 to remain in contact with the surface 400 at all times. In this instance it is preferable to place the core samples on a small V-bench to acquire greater access to the core 300.

Referencing

Placing the apparatus 10 on the core 300 where the vertical orientation plane intersects the upper or lower surface of the core 300, commonly referred to as the Top Of Core Line (TOC) or Bottom of Core line (BOC) line 106 and pressing the referencing button 28.1, initially aligns/references the apparatus 10 in relation to the core 300. This position can be referred to as the reference point/position. The precise geometric disposition of the orientation line can be determined by using commercially available down-the-hole gyroscopic survey devices.

The disposition of the vertical orientation plane can be determined using commercially available down-the-hole orientation instruments.

Accurate measurements of a structural feature 600 are obtained by recording several measurements of the feature 600 on the surface 400 of the core 300. The software statistically analyses the data and produces the best fit estimation of the orientation of the structural feature 600. This feature of the software can also be used to analyse the orientation of the same repetitive structural feature 600, such as bedding or fore sets (which are spaced along the length of the core). The program will calculate the best fit or average orientation of the measured structural features 600. Every section of continuous orientated core should be referenced and coordinated by the apparatus 10.

Procedure for Recording Planar Structural Features i. Reference the apparatus 10 by placing it on the core 300 parallel to the BOC orientation line 106, with the point 17 positioned over a particular depth mark generally indicated by reference numeral 104 in FIGS. 16 and 17. Press the referencing button 28.1 and enter the depth into the computer 200 (or tablet 202).

ii. Align the apparatus 10 with a plane 102 of the structural feature 600 (see FIGS. 16 and 17). This can be done in two ways:

a. For open/exposed planar features, place the apparatus 10 with the guide formations 22.1, 22.2 resting on the plane 102, press the button 28.3 to record the reading. For more accurate recordings a number of readings can be entered at different positions on the plane 102.

b. For unexposed planar features, place the point 17 on any position where a trace of the structural feature is exposed/outcrops on the surface 400 of the core 300, the laser beam/diodes 38, 40 turn on/off automatically once the alignment method is selected, and rotate the apparatus 10 until the laser beams 41, 43 project along the trace of the structure. Then, press the record button 28.3.

For more accurate planar recordings, after referencing, the apparatus 10 can be moved along the surface 400 such that the point 17 is placed at a position where the feature 600 intersects the surface 400. The button 28.3 is then pressed. (It should be noted that this is not the so-called 'Top of Ellipse' as defined in the Internal Core Angles Method.) Repeat this on at least four different points along the feature trace. It is imperative for the optical sensor 29 to work properly and that the apparatus 10 remains on the core surface 400 at all times. The apparatus 10 should be returned to the original reference point to complete the recording.

Linear Structures

As mentioned above, the apparatus 10 utilises the optical sensor 29 to record the real-space orientation of linear structural features 600 (e.g. slickenside striae, fold axes, crenulations, mullions and deformed pebbles) in cores accurately. Even the so-called Line of Intersection (LOI) between two planar structures can be determined using the apparatus 10. To be able to take readings, the core samples should preferably be removed from the core tray and placed on a small V-bench. The measurements are made directly off the surface 400 and are accurate even for structural features at high core angles, i.e. at angles greater than 60° from the plane to the core axis. Detailed and comprehensive microstructural analyses of individual core samples may also be performed.

Procedure for Recording Linear Structural Features

Figure 18:
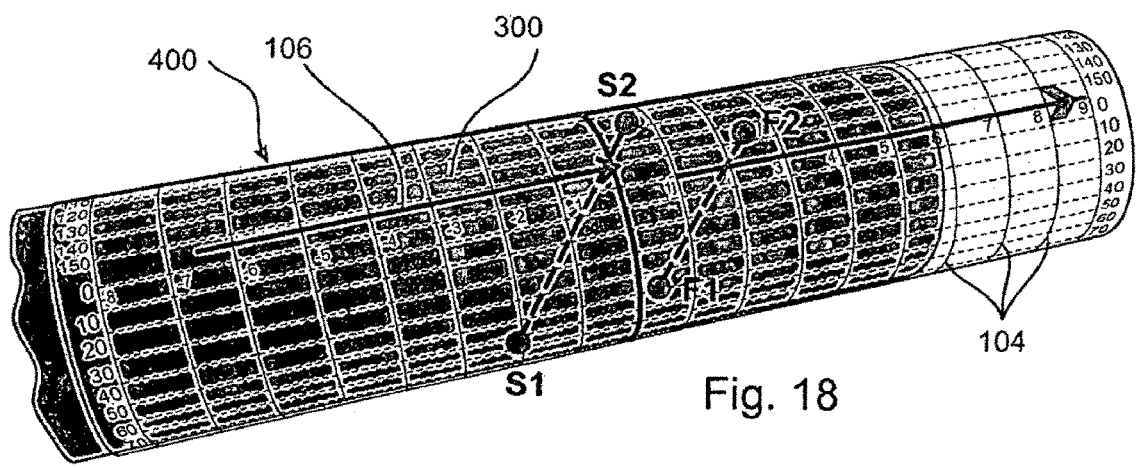
FIG. 18 shows a three-dimensional view of a borehole core indicating possible recording positions to obtain accurate information when recording a linear structural feature.

Reference is now specifically made to FIG. 18.

i. The apparatus 10 by placing it on the surface 400 of the core 300 parallel to the BOC orientation line 106 with the point 17 positioned over a particular depth mark. Press the button 28.1 and enter the depth into the computer 200.

ii. With the apparatus 10 remaining in contact with the surface 400 at all times, move the apparatus along the surface 400 and place the point 17 at the position where the feature 600 intersects the surface 400 (see S1). Then press the button 28.3.

iii. Move the apparatus over the surface 400 to another position where the linear feature intersects the surface 400 (see S2). Again press the button 28.3. (It should be noted that either end of the linear feature, S1 or S2, can be used as the initial reference point (in step ii)).
iv. A number of structures can be logged in this way. The process ends once the apparatus 10 is returned to the original reference point captured in step i.

If there is any evidence of displacement (i.e. slickensides), a side of the apparatus 10 can also be used as a reference to orientate the tool.

In situations where the sense of shear (SOS) can be determined from structures, e.g. with slickensides on a fault surface, the direction of displacement can be recorded and input into the program, so that a detailed kinematic analysis of the core can be conducted. The program plots the directional linear feature as an arrow on the plate representing the planar structure.

Magnetic Susceptibility Recordings
i. Reference the apparatus 10 by placing it on the surface 400 of the core 300 parallel to the BOC orientation line 106 with the point 17 positioned over a particular depth mark. Press the referencing button 28.1 and enter the depth into the computer 200.
ii. With the apparatus 10 remaining in contact with the surface 400 at all times move the apparatus 10 along the surface 400 and place the point 17 at the position where a magnetic reading needs to be taken and press the button 28.3.
iii. Move the apparatus 10 over the surface 400 and take two additional readings on either side of the core 300 at the same depth as the position mentioned in step ii.
iv. The captured data is sent directly to the software (which is installed on the computer 200) which then determines the direction of the remnant magnetism.

The apparatus 10 is a geotechnical handheld sampling tool which is capable of measuring and computing the geometrical disposition of planar and linear structural features exhibited in orientated borehole core samples. The Inventors believe that the system 100 and apparatus 10 simplify and enhance geotechnical mapping of structures in borehole cores.

The system 100 and apparatus 10 also offer an interactive and quantitative technique for logging structures and generally do not require specialized training or an in-depth understanding of stereographic analysis. Down-hole surveys and geological and structural logs can be imported, processed and then exported in spreadsheet or text format into geologic processing or mine planning software programs. Data so acquired may alternatively, or additionally, be transferred to cloud-based storage.

The apparatus 10 has the capability of recording the orientation of structural features 600 in core samples directly off the core 300. By clicking once on the depth along the orientation line 106 and then at three positions on the structural plane (for a planar feature) or at just two positions (for a linear feature), the system 10 can immediately (in real-time) calculate and display the orientation of the feature 600 on a computer 200 or tablet 202. The real space orientation of the structural feature 600 is immediately presented to the geologist in three-dimensional orthographic or stereographic projection at the time of logging the core 300.

The invention described above has a number of advantages over existing systems. One of the main advantages is that the 'real space' orientations of structural elements in core samples are automatically calculated and presented in 3D orthographic projection to the geologist at the time of logging (i.e. there is no transposing or recalculations).

Individual datum points can also be checked and verified prior to input. The invention is also relatively simple in that the measurements are recorded directly off the surface 400 of the core 300 and does not require the use of measuring templates. There is also generally no rounding of the estimated measurements. Borehole survey data together with geotechnical/geological borehole logs can also be imported and/or exported in spreadsheet or text format, as well as optionally being transferred to cloud based storage. The accurate recording of structures and measurements are not reliant on the determination of the ellipse, as in the Internal Angles method. Even structures at high alpha angles can be accurately determined.

The Inventors also believe that the invention provides a relatively simple measuring technique. The invention simply utilizes the down-hole depth and the offset along the left and right-hand side of the core 300 to determine the orientation of the planar structures. Linear structures require the offsets combined with the rotation angle that can be recorded using a simple template.

The invention is also relatively inexpensive, since no expensive goniometers are used. The invention also saves time since the capturing of the data is faster.

In the first embodiment, the beam-forming arrangement 35 comprises two line laser diodes 38, 40 are mounted on respective sides of a front part of the base 16 Other beam-forming arrangement are, of course possible, one example of which is featured in a second embodiment of apparatus 10

Figure 28:
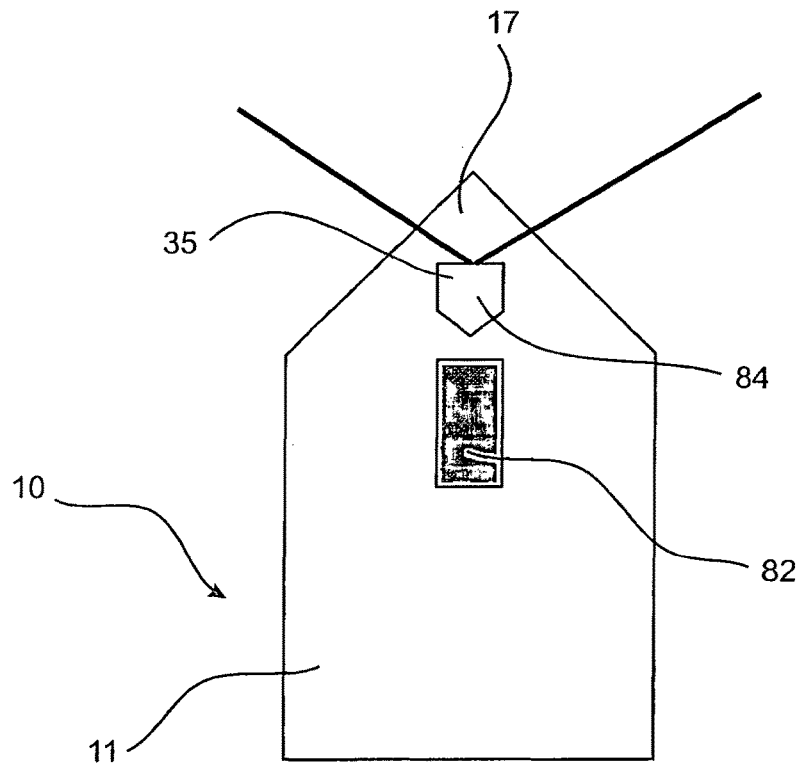
FIG. 28 shows a schematic top view of a second embodiment of apparatus according to the invention.
Figure 29:
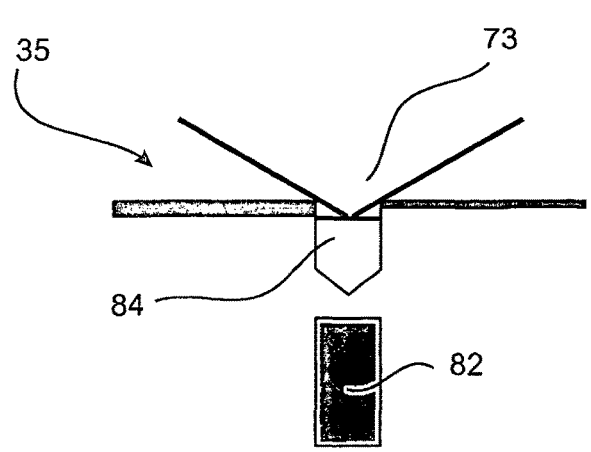
FIG. 29 shows a schematic plan view of an arrangement for emitting the laser beam as depicted in FIG. 28.
Figure 30:
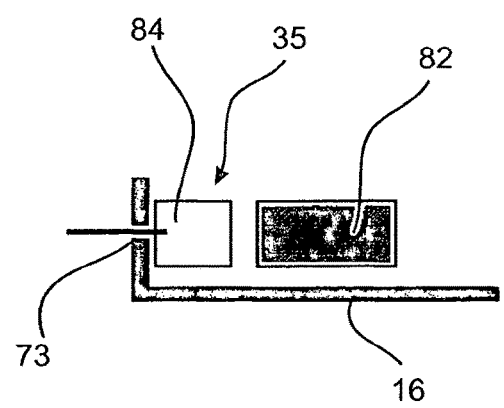
FIG. 30 shows a schematic side view of the arrangement for emitting the laser beam as depicted in FIG. 28.

Referring now to FIGS. 28 to 30, there is shown (schematically) a second embodiment of apparatus 10. The second embodiment of apparatus 10 is similar in many respects to the first embodiment described and illustrated previously, and so corresponding reference numerals are used to denote similar parts.

In this second embodiment, the beam-forming arrangement 35 comprises a centrally located laser module 82 and associated dispersion lens 84 operable to emit a beam of light for projection onto the surface 400 of the core 300 to provide a visual indication on the surface for alignment purposes. In the arrangement shown, the dispersion lens 84 comprises a Powell lens, or other similar lens, capable of providing a more evenly lit indication line and a generally wider angle of projection of the beam. In this embodiment, the beam width is about 120 degrees. An advantage of the arrangement of this second embodiment in comparison to the first embodiment is that there is a single beam emitted, thereby avoiding the need to align two separate beams on opposed sides of the apparatus 10 with the pointer 17.

It should be appreciated that the scope of the invention is not limited to the scope of the two embodiments described. Modifications and variations such as would be apparent to the skilled addressee are considered to fall within the scope of the present invention.

The present disclosure is provided to explain in an enabling fashion the best modes of making and using various embodiments in accordance with the present invention. The disclosure is further offered to enhance an understanding and appreciation for the invention principles and advantages thereof, rather than to limit in any manner the invention. While a preferred embodiment of the invention has been described and illustrated, it is clear that the invention is not so limited. Numerous modifications, changes, variations, substitutions, and equivalents will occur to those skilled in the art having the benefit of this disclosure without departing from the spirit and scope of the present invention as defined by the following claims.

Reference to positional descriptions, such as "inner", "outer", "upper", "lower", "top" and "bottom", are to be taken in context of the embodiments depicted in the drawings, and are not to be taken as limiting the invention to the literal interpretation of the term but rather as would be understood by the skilled addressee.

Additionally, where the terms "system", "device", and "apparatus" are used in the context of the invention, they are to be understood as including reference to any group of functionally related or interacting, interrelated, interdependent or associated components or elements that may be located in proximity to, separate from, integrated with, or discrete from, each other.

Throughout this specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. A method of determining the disposition and or orientation of structural feature(s) present in a borehole core, wherein the method comprises:
holding an apparatus by hand;
moving by hand the apparatus, or part thereof, relative to a structural feature present in the core, the apparatus or part thereof in contact with a surface of the core and orienting the apparatus by hand angularly relative to an axis of the core about a fulcrum to align a body of the apparatus with the structural feature;
capturing data on the movement and angular orientation of the apparatus, or the part thereof, as or when it is moved or oriented in relation to the structural feature and core, by using a movement or orientation arrangement of the apparatus; and
determining, by using a processor, the orientation or disposition of the structural feature in relation to the core, by utilizing the captured data.

2. The method according to claim 1, further comprising: (a) visually displaying the orientation or disposition of the structural feature in relation to the core on a display; or (b) transferring data relating to the orientation or disposition of the structural feature in relation to the core to a remote server; or (c) transferring data from a point of acquisition to cloud-based storage or (d) determining, by using a processor, the change in orientation of the apparatus, or a part thereof, between a reference orientation and the orientation when it is aligned with the structure, or the part thereof.

3. The method according to claim 1, wherein the step of determining the orientation or disposition of the structural feature comprises determining the real space orientation or disposition in relation to the core.

4. The method according to claim 1, wherein the step of moving an apparatus comprises: performing one of (a) aligning the apparatus, or a part thereof, with the structural feature, or a specific part portion thereof; or (b) aligning the apparatus, or the part thereof, with a surface of the structural feature if the feature is a planar feature or (c) moving the apparatus over an outer surface of the core in order to align the apparatus, or part thereof, with at least one part of the structure which is exposed on the outer surface, and then (d) angularly moving the body to align with a plane of the planar feature transverse to the core axis, and the step of capturing data comprises capturing position and orientation data of the apparatus once aligned.

5. The method according to claim 1, wherein the step of determining the orientation of the structural feature in relation to the core comprises determining the movement or orientation of the apparatus in relation to a reference point or orientation.

6. The method according to claim 5, wherein the step of determining the movement of the apparatus in relation to a reference point or orientation comprises determining a reference point or orientation in relation to the core.

7. The method according to claim 1, wherein the step of orienting the apparatus by hand angularly further comprises aligning the apparatus, or part thereof, with the surface by aligning an alignment indicator with the surface of the feature.

8. The method according to claim 7, wherein the step of aligning an alignment indicator with the surface of the feature alignment indicator comprises providing a visual indication on the surface of the core and aligning the visual indication with the surface of the feature.

9. The method according to claim 8, wherein the step of providing a visual indication on the surface of the core comprises projecting a beam of light from the apparatus.

10. The method according to claim 8, wherein aligning the apparatus, or the part thereof, with the surface comprises aligning a beam of light which is projected from the apparatus with the surface.

11. The method according to claim 1, wherein the step of capturing the data comprises aligning the apparatus, or part thereof, with two or more parts of the structure which are exposed on the outer surface, and to each time capture orientation data once aligned.

12. The method according to claim 1, wherein the step of visually displaying the orientation or disposition of the structural feature comprises displaying the orientation or disposition of the structural feature in real time as soon as the data has been captured and the orientation or disposition of the structural feature in relation to the core sample has been determined.

13. The method according to claim 1 comprising moving or orienting the apparatus relative to the core while the core is in a core tray.

14. An apparatus for capturing data on structural features present in a borehole core sample having a circular outer periphery defining an outer surface and a central longitudinal axis defining a core axis, wherein the apparatus comprises:
an orientation arrangement which is configured to determine the angular orientation, or change in orientation, of the apparatus, or part thereof with respect to the core axis;
a data-capturing arrangement which is configured to capture orientation data generated by the orientation arrangement;
a body that houses the orientation arrangement and the data-capturing arrangement, wherein the body is arranged to be held, moved and manipulated by a hand of a user; and
an alignment arrangement having a fulcrum and a laser designator providing a sensing beam operable to manually angularly align the body about the fulcrum with a structural feature of the core, wherein the structural feature is transverse to the core axis whereby the orientation arrangement measures angle data of the structural feature and the data-capturing arrangement records the angle data.

15. The apparatus according to claim 14 wherein the alignment arrangement comprises a beam-forming arrangement which is configured to emit at least one beam, when in use, which provides the sensing beam to align the apparatus with the structural feature.

16. The apparatus according to claim 14, wherein the orientation arrangement comprises at least one of a gyroscope, an accelerometer, an optical sensor and a magnetometer.

17. The apparatus according to claim 14, further comprising a communication arrangement configured to send orientation data to a processing arrangement.

18. The apparatus according to claim 14, further comprising at least one guide formation configured to guide displacement of the apparatus over an outer surface of a core.

19. The apparatus according to claim 18, comprising a pair of guide formations.

20. The apparatus according to claim 14 wherein the body comprises a base portion adapted for movement over the outer surface to determine the distance between two measurement points on the outer surface, and wherein the fulcrum of the alignment arrangement presents a reference for aligning the body with a plane transverse to the central longitudinal axis, the alignment arrangement capable of providing a visual indication on the surface of the core sample, whereby an indication of the angular disposition of the plane can be obtained by the angle data relative to the central longitudinal axis.

21. The apparatus according to claim 14 wherein, the body comprises a base portion adapted for movement over the outer surface, the base portion being configured as a saddle for location on an outer surface of the core sample and sliding movement over the outer surface, and wherein the fulcrum of the alignment arrangement presents a reference for aligning the body with a plane transverse to the central longitudinal axis, whereby an indication of the angular disposition of the plane can be obtained by the angle data relative to the central longitudinal axis.

22. The apparatus according to claim 20 further comprising a contact portion for contacting the outer surface of the core sample while moving the body angularly with respect to the central longitudinal axis of the core sample to align the body with a plane transverse to the central longitudinal axis.

23. The apparatus according to claim 20 wherein the fulcrum comprises a locator for positioning the base portion with respect to a mark or feature of an outer surface of the core sample.

24. The apparatus according to claim 21, wherein the fulcrum comprises a locator for positioning the base portion with respect to a mark or feature of an outer surface of the core sample.

25. A system for determining the disposition or orientation of structural features present in a borehole core, wherein the system comprises:
 an apparatus having an orientation arrangement which is configured to determine the angular orientation, or change in angular orientation with respect to an axis of the borehole core, of the apparatus, or part thereof;
 a data-capturing arrangement which is configured to capture orientation data generated by the orientation arrangement;
 a body which houses the orientation arrangement and the data-capturing arrangement, and wherein the body is arranged to be held, moved and manipulated by a hand of a user;
 an alignment arrangement having a fulcrum and a laser designator providing a sensing beam operable to manually angularly align the body about the fulcrum with a structural feature of the core, wherein the structural feature is transverse to the core axis whereby the orientation arrangement measures angle data of the structural feature and the data-capturing arrangement records the angle data;
 a processing arrangement which is connected to, or forms part of, the apparatus, and which is configured to determine at least the orientation of the structural feature in relation to the borehole core, by utilizing at least the angle data.

26. The system according to claim 25, further comprising a display arrangement configured to present a visual simulation of the orientation of the structural feature in relation to the borehole core.

27. The system according to claim 25, wherein the processing arrangement comprises a communications enabled computing device configured for transfer of data to cloud-based storage.

28. The system according to claim 25, wherein the processing arrangement comprises a communications enabled computing device separate from the apparatus and arranged to communicate with the apparatus.

29. The system according to claim 28, comprising a visual display device connected to the communications enabled computing device.

* * * * *